United States Patent
Scheunemann et al.

(10) Patent No.: US 6,660,728 B2
(45) Date of Patent: Dec. 9, 2003

(54) THIENYL SUBSTITUTED ACYLGUANIDINES AS INHIBITORS OF BONE RESORPTION AND VITRONECTIN RECEPTOR ANTAGONISTS

(75) Inventors: Karl-Heinz Scheunemann, Liederbach (DE); Jochen Knolle, Frankfurt am Main (DE); Amuschirwan Peyman, Kelheim (DE); David William Will, Kriftel (DE); Denis Carniato, Cagnes sur Mer (FR); Jean-Francois Gourvest, Claye Souilly (FR); Thomas Gadek, Oakland, CA (US); Robert McDowell, San Fransicso, CA (US); Sarah Catherine Bodary, San Bruno, CA (US); Robert Andrew Cuthbertson, Victoria (AU)

(73) Assignees: Aventis Pharma Deutschland GmbH (DE); Genentech, Inc.

( * ) Notice: Subject to any disclaimer, the term of this patent is extended or adjusted under 35 U.S.C. 154(b) by 0 days.

(21) Appl. No.: 10/368,771

(22) Filed: Nov. 14, 2002

(65) Prior Publication Data

US 2003/0153557 A1 Aug. 14, 2003

Related U.S. Application Data

(62) Division of application No. 09/700,655, filed as application No. PCT/EP99/03064 on May 5, 1999, now Pat. No. 6,566,366.

(30) Foreign Application Priority Data

May 19, 1998 (EP) .............................................. 98109077

(51) Int. Cl.[7] ........................ A61K 31/33; A61K 31/38; A61K 31/335; C07D 213/00; C07D 317/00
(52) U.S. Cl. ........................ 514/183; 514/277; 514/438; 514/448; 514/449; 514/463; 514/464; 546/1; 546/329; 546/339; 549/74; 549/75; 549/76; 549/79; 549/200; 549/429; 549/434; 549/469
(58) Field of Search .................. 514/183, 277, 514/438, 448, 449, 463, 464; 546/1, 329, 339; 549/74, 75, 76, 79, 200, 429, 434, 469

(56) References Cited

FOREIGN PATENT DOCUMENTS

EP 820991 * 1/1998

* cited by examiner

*Primary Examiner*—Richard L.. Raymond
*Assistant Examiner*—Sudhaker B. Patel
(74) *Attorney, Agent, or Firm*—Muserlian, Lucas and Mercanti

(57) ABSTRACT

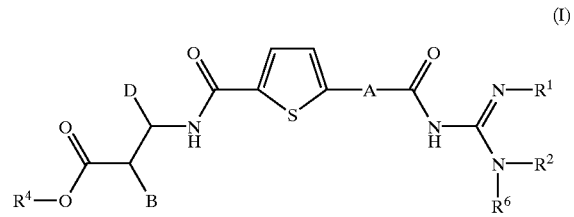

The present invention relates to thienyl substituted acylguanidine derivatives, such as compounds of formula (I) in which $R^1$, $R^2$, $R^4$, $R^6$, A, B and D have the meanings indicated in the claims, their physiologically tolerable salts and their prodrugs. The compounds of the present invention are valuable pharmaceutical active compounds. They are vitronectin receptor antagonists and inhibitors of bone resorption by osteoclasts. They are suitable, for example, for the therapy and prophylaxis of diseases which are caused at least partially by an undesired extent of bone resorption, for example of osteoporosis. The invention furthermore relates to processes for the preparation of thienyl substituted acylguanidines, their use, in particular as active ingredients in pharmaceuticals, and pharmaceutical preparations comprising them.

8 Claims, No Drawings

THIENYL SUBSTITUTED ACYLGUANIDINES AS INHIBITORS OF BONE RESORPTION AND VITRONECTIN RECEPTOR ANTAGONISTS

PRIOR APPLICATIONS

This application is a division of U.S. patent application Ser. No. 09/700,655 filed Mar. 6, 2001, now U.S. Pat. No. 6,566,366 which is a 371 of PCT/EP99/03064 filed May 5, 1999.

The present invention relates to thienyl substituted acylguanidine derivatives, such as compounds of the formula I

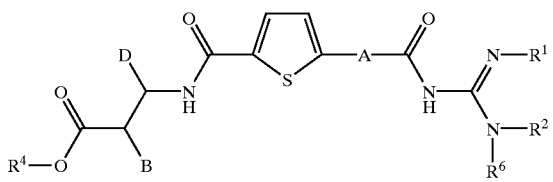

in which $R^1$, $R^2$, $R^4$, $R^6$, A, B und D have the meanings indicated below, their physiologically tolerable salts and their prodrugs. The compounds of the present invention are valuable pharmaceutical active compounds. They are vitronectin receptor antagonists and inhibitors of bone resorption by osteoclasts. They are suitable, for example, for the therapy and prophylexis of diseases which are caused at least partially by an undesired extent of bone resorption, for example of osteoporosis. The invention furthermore relates to processes for the preparation of thienyl substituted acylguanidines, their use, in particular as active ingredients in pharmaceuticals, and pharmaceutical preparations comprising them.

Human bones are subject to a constant dynamic renovation process comprising bone resorption and bone formation. These processes are controlled by types of cell specialized for these purposes. Bone resorption is based on the destruction of bone matrix by osteoclasts. The majority of bone disorders are based on a disturbed equilibrium between bone formation and bone resorption. Osteoporosis is a disease characterized by low bone mass and enhanced bone fragility resulting in an increased risk of fractures. It results from a deficit in new bone formation versus bone resorption during the ongoing remodeling process. Conventional osteoporosis treatment includes, for example, the administration of bisphosphonates, estrogens, estrogen/progesterone (hormone replacement therapy or HRT), estrogen agonists/antagonists (selective estrogen receptor modulators or SERMs), calcitonin, vitamin D analogues, parathyroid hormone, growth hormone secretagogues, or sodium fluoride (Jardine et al., Annual Reports in Medicinal Chemistry 1996, 31, 211).

Activated osteoclasts are polynuclear cells having a diameter of up to 400 μm which remove bone matrix. Activated osteoclasts become attached to the surface of the bone matrix and secrete proteolytic enzymes and acids into the so-called "sealing zone", the region between their cell membrane and the bone matrix. The acidic environment and the proteases cause the destruction of the bone. The compounds of the present invention inhibit bone resorption by osteoclasts.

Studies have shown that the attachment of osteoclasts to the bones is controlled by integrin receptors on the cell surface of osteoclasts. Integrins are a superfamily of receptors which include, inter alia, the fibrinogen receptor $\alpha_{IIb}\beta_3$ on blood platelets and the vitronectin receptor $\alpha_v\beta_3$. The vitronectin receptor $\alpha_v\beta_3$ is a membrane glycoprotein which is expressed on the cell surface of a number of cells such as endothelial cells, cells of the vascular smooth musculature, osteoclasts and tumor cells. The vitronectin receptor $\alpha_v\beta_3$, which is expressed on the osteoclast membrane controls the process of osteoclasts attachment to the bones and bone resorption, and thus contributes to osteoporosis. $\alpha_v\beta_3$ in this case binds to bone matrix proteins such as osteopontin, bone sialoprotein and thrombospondin which contain the tripeptide motif Arg-Gly-Asp (or RGD).

Horton and coworkers describe RGD peptides and an anti-vitronectin receptor antibody (23C6) which inhibit tooth destruction by osteoclasts and the migration of osteoclasts (Horton et al., Exp. Cell. Res. 1991, 195, 368). In J. Cell Biol. 1990, 111, 1713, Sato et al. describe echistatin, an RGD containing peptide from snake venom, as a potent inhibitor of bone resorption in a tissue culture and as an inhibitor of osteoclast adhesion to the bones. Fisher et al. (Endocrinology 1993, 132, 1411) were able to show in the rat that echistatin also inhibits bone resorption in vivo. Yamamoto et al. (Endocrinology 1998, 139, 1411) show that echistatin prevents bone loss in ovarectomized mice and rats.

It was furthermore shown that the vitronectin $\alpha_v\beta_3$ on human cells of the vascular smooth musculature of the aorta stimulates the migration of these cells into the neointima, which finally leads to arteriosclerosis and restenosis after angioplasty (Brown et al., Cardiovascular Res. 1994, 28, 1815). Yue et al. (Pharmacology Reviews and Communications 1998, 10, 9) show the inhibition of neointima formation using an $\alpha_v\beta_3$ antagonist.

Brooks et al. (Cell 1994, 79, 1157) showed that antibodies against $\alpha_v\beta_3$ or $\alpha_v\beta_3$ antagonists can cause a shrinkage of tumors by inducing the apoptosis of blood vessel cells during angiogenesis. The vitronectin receptor $\alpha_v\beta_3$ is also involved in the progression of a variety of other types of cancer, and is overexpressed in malignant melanoma cells (Engleman et al., Annual Reports in Medicinal Chemistry 1996, 31, 191). The melanoma invasiveness correlated with this overexpression (Stracke et al., Encyclopedia of Cancer, volume III, 1855, Academic Press 1997; Hillis et al., Clinical Science 1996, 91, 639). Carron et al. (Cancer Res. 1998, 58, 1930) describe the inhibition of tumor growth and the inhibition of hypercalcemia of malignancy using an $\alpha_v\beta_3$ antagonist.

Friedlander et al. (Science 1995, 270, 1500) describe anti-$\alpha_v\beta_3$ antibodies or $\alpha_v\beta_3$ antagonists which inhibit the bFGF-induced angiogenesis processes in the rat eye, a property which can be used therapeutically in the treatment of retinopathies. Storgard et al. (J. Clin. Invest. 1999, 103, 47) describe the use of $\alpha_v\beta_3$ antagonists in the treatment of arthritic diseases. Hammes et al. showed that cyclic peptidic $\alpha_v\beta_3$ antagonists inhibit angiogenesis in an ischemic model of retinopathy (Nature Medicine 1996, 2, 529). Influencing of the vitronectin receptor or of the interactions in which it is involved thus offers the possibility of influencing different disease states for whose therapy and prophylaxis there continues to be a need for suitable pharmaceutical active ingredients.

Patent application WO-A-94/12181 describes substituted aromatic or nonaromatic ring systems, and WO-A-94/08577 describes substituted heterocycles as fibrinogen receptor antagonists and inhibitors of platelet aggregation. EP-A-528586 and EP-A-528587 disclose aminoalkyl-substituted or heterocyclyl-substituted phenylalanine derivatives, and WO-A-95/32710 discloses aryl derivatives as inhibitors of bone resorption by osteoclasts. WO-A-96/00574 describes benzodiazepines, and WO-A-96/00730 describes fibrinogen receptor antagonist templates, in particular benzodiazepines which are linked to a nitrogen-bearing 5-membered ring, as vitronectin receptor antagonists. EP-A-820991 discloses cycloalkyl derivatives, international patent application PCT/EP98/08051 discloses carbamic ester derivatives and international patent application PCT/EP99/00242 discloses sulfonamides which are vitronectin receptor antagonists. Certain thiophene derivatives which are potent and selectively acting fibrinogen receptor antagonists are disclosed in WO-A-94/08577. Further investigations have shown that the thienyl substituted acylguanidines of the present invention are particularly strong inhibitors of the vitronectin receptor and of bone resorption by osteoclasts.

Thus, a subject of the present invention are compounds of the formula I,

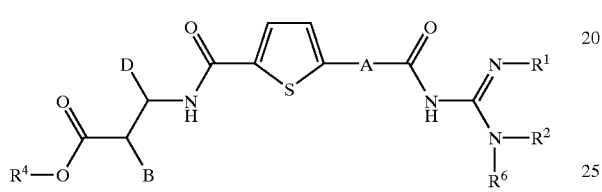

I in which

A is a saturated or unsaturated bivalent $(C_1-C_9)$-alkylene residue or a bivalent $(C_3-C_7)$-cycloalkylene residue, wherein the alkylene residue and the cycloalkylene residue each is unsubstituted or is substituted by one or more residues from the series consisting of halogen, $(C_1-C_6)$-alkyl, $(C_1-C_6)$-alkoxy, $(C_6-C_{14})$-aryl, $(C_6-C_{14})$-aryl-$(C_1-C_6)$-alkyl-, $(C_5-C_{14})$-heteroaryl, $(C_5-C_{14})$-heteroaryl-$(C_1-C_6)$-alkyl-, $(C_3-C_{12})$-cycloalkyl, $(C_3-C_{12})$-cycloalkyl-$(C_1-C_5)$-alkyl- and oxo;

B is hydrogen, $-NH-CO-OR^5$, $-NH-SO_2-R^5$, $-NH-SO_2-(C_6-C_{14})$-aryl, $-NH-SO_2-(C_5-C_{14})$-heteroaryl, $-NH-CO-R^5$, $-NH-CO-(C_6-C_{14})$-aryl, $-NH-CO-(C_5-C_{14})$-heteroaryl, $-NH-CO-NH-R^5$, $-NH-CO-NH-(C_6-C_{14})$-aryl, $-NH-CO-NH-(C_5-C_{14})$-heteroaryl, $-NH-SO_2-NH-R^5$, $-NH-SO_2-NH-(C_6-C_{14})$-aryl or $-NH-SO_2-NH-(C_5-C_{14})$-heteroaryl;

D is hydrogen, $(C_6-C_{14})$-aryl, $(C_5-C_{14})$-heteroaryl or $R^5$;

$R^1$ and $R^2$ independently of one another are hydrogen or $(C_1-C_6)$-alkyl which is unsubstituted or substituted by one or more residues $R^3$, or $R^1$ and $R^2$ together are a saturated or unsaturated bivalent $(C_2-C_9)$-alkylene residue which is unsubstituted or is substituted by one or more residues from the series consisting of halogen, $(C_1-C_6)$-alkyl, $(C_1-C_6)$-alkoxy, $(C_6-C_{14})$-aryl, $(C_6-C_{14})$-aryl-$(C_1-C_6)$-alkyl-, $(C_5-C_{14})$-heteroaryl, $(C_5-C_{14})$-heteroaryl-$(C_1-C_6)$-alkyl-, $(C_3-C_{12})$-cycloalkyl, $(C_3-C_{12})$-cycloalkyl-$(C_1-C_6)$-alkyl- and oxo, where a 5- to 7-membered saturated or unsaturated ring which is unsubstituted or is substituted by one or more residues $R^3$ and which is a carbocyclic ring or a heterocyclic ring containing one or two ring nitrogen atoms, can be fused to a carbon—carbon bond in the $(C_2-C_9)$-alkylene residue;

$R^3$ is $(C_1-C_8)$-alkyl, $(C_1-C_8)$-alkoxy, $(C_5-C_{14})$-aryl, $(C_5-C_{14})$-aryl-$(C_1-C_4)$-alkyl-, halogen, trifluoromethyl, hydroxyl, nitro or amino;

$R^4$ is hydrogen, $(C_1-C_5)$-alkyl-CO—O—$(C_1-C_4)$-alkyl- or $(C_1-C_6)$-alkyl which is unsubstituted or is substituted by a residue from the series consisting of hydroxyl, $(C_1-C_4)$-alkoxy, $(C_1-C_4)$-alkyl-S(O)$_2-$, $-NR^7R^{7a}$ and $-N^+R^7R^{7a}R^{7b}Q^-$, where $R^7$, $R^{7a}$ and $R^{7b}$ independently of one another are hydrogen, $(C_1-C_6)$-alkyl, $(C_5-C_{14})$-aryl or $(C_5-C_{14})$-aryl-$C_1-C_6)$-alkyl- and $Q^-$ is a physiologically tolerable anion, or $R^4$ is one of the residues

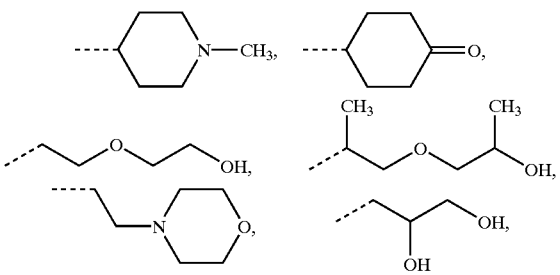

in which the bonds via which the residues are bonded, are indicated by dashed lines;

$R^5$ is $(C_1-C_{14})$-alkyl, $(C_3-C_{12})$-cycloalkyl, $(C_3-C_{12})$-cycloalkyl-$(C_1-C_6)$-alkyl-, $(C_6-C_{14})$-aryl-$(C_1-C_6)$-alkyl- or $(C_5-C_{14})$-heteroaryl-$(C_1-C_6)$-alkyl-, where the $(C_1-C_{14})$-alkyl residue is unsubstituted or substituted by one or more halogen atoms and where the aryl residue and the heteroaryl residue is unsubstituted or is substituted by one or more residues $R^3$;

$R^6$ is hydrogen, $(C_1-C_6)$-alkyl-O—CO—, hydroxyl, $(C_1-C_6)$-alkyl-O—CO—O— or nitro;

in all their stereoisomeric forms and mixtures thereof in all ratios, and their physiologically tolerable salts and their prodrugs.

In addition to the compounds of the formula I in which the two residues bonded to the central thiophene ring are bonded to the 2-position and the 5-position of the thiophene ring, a further subject of the present invention are the positional isomers of the compounds of the formula I with a different substitution pattern on the central thiophene ring. For example, a subject of the present invention are compounds in which one of the two residues bonded to the central thiophene ring in the formula I is bonded to the 2-position of the thiophene ring and the other is bonded to the 4-position of the thiophene ring, including the isomer in which the residue $R^4O-CO-CHB-CHD-NH-CO-$ is bonded to the 2-position and the residue $R^6R^2N-C(=NR^1)-NH-CO-A-$ is bonded to the 4-position, as well as the isomer in which the residue $R^6R^2N-C(=NR^1)-NH-CO-A-$ is bonded to the 2-position and the residue $R^4O-CO-CHB-CHD-NH-CO-$ is bonded to the 4-position. Further, a subject of the present invention are, for example, compounds in which one of the two residues bonded to the central thiophene ring in the formula I is bonded to the 3-position of the thiophene ring and the other is bonded to the 4-position of the thiophene ring. In addition, compounds of the formula I and positional isomers thereof in which the central thiophene ring carries one or two further substituents, for example identical or different $(C_1-C_4)$-alkyl groups and/or halogen atoms, form a part of the present invention. All statements above and below relating to the compounds of the formula I also apply to such positional isomers of the compounds of the formula I and to such analogues substituted on the thiophene ring which form a part of the present invention. Whenever in the following statements are made with respect to the compounds of the formula I, such positional isomers with a different substitution pattern and such substituted analogues have expressly to be understood as being included.

All residues which can occur several times in the compounds of the formula I, for example substituents present in groups like alkyl groups, alkylene groups, aryl groups, etc., or residues like $R^3$, $R^5$ etc., can each independently of one another have the meanings indicated. All such residues can each be different or identical.

Alkyl residues can be straight-chain or branched, saturated or mono- or polyunsaturated. This also applies if they carry substituents or occur as substituents of other residues, for example in alkoxy residues, alkoxycarbonyl residues or arylalkyl residues. The same applies to alkylene residues. Examples of suitable alkyl residues are methyl, ethyl, propyl, butyl, pentyl, hexyl, heptyl, octyl, nonyl, decyl, undecyl, dodecyl, tridecyl, tetradecyl, hexadecyl, octadecyl, including the n-isomers of all these alkyl residues as well as, for example, isopropyl, isobutyl, isopentyl, neopentyl, isohexyl, 3-methylpentyl, 2,3,4-trimethylhexyl, sec-butyl, tert-butyl, tert-pentyl. Preferred alkyl residues are methyl, ethyl, n-propyl, isopropyl, n-butyl, isobutyl, sec-butyl and tert-butyl. The bivalent residues corresponding to the abovementioned monovalent residues, for example methylene, ethylene, 1,3-propylene, 1,2-propylene (=methylethylene), 2,3-butylene (=1,2-dimethylethylene), 1,4-butylene, 1,6-hexylene, are examples of alkylene residues (=alkanediyl residues).

Unsaturated alkyl residues are, for example, alkenyl residues such as vinyl, 1-propenyl, allyl, butenyl, 3-methyl-2-butenyl, or alkynyl residues such as ethynyl, 1-propynyl or propargyl. Unsaturated alkylene residues such as alkenylene residues (=alkenediyl residues) and alkynylene residues (=alkynediyl residues) can likewise be straight-chain or branched. Examples of alkenylene residues are vinylene, propenylene or 2-butenylene, examples of alkynylene residues are ethynylene or propynylene.

Cycloalkyl residues can be monocyclic, bicyclic, tricyclic, tetracyclic or pentacyclic, provided that they contain a suitable number of carbon atoms and the parent polycyclic hydrocarbon system is stable. Monocycloalkyl residues are, in particular, cyclopropyl, cyclobutyl, cyclopentyl, cyclohexyl, cycloheptyl, cyclooctyl, cyclononyl, cyclodecyl, cycloundecyl or cyclododecyl, which can be unsubstituted but can also be substituted by one or more identical or different residues, for example by $(C_1-C_4)$-alkyl residues like methyl. Examples of substituted monocycloalkyl residues which may be mentioned are 4-methylcyclohexyl or 2,3-dimethylcyclopentyl. The bivalent residues corresponding to the abovementioned monovalent residues, for example 1,2-cyclopropylene, 1,2-cyclobutylene, 1,2-cyclopentylene, 1,2-cyclohexylene, 1,2-cycloheptylene, 1,3-cyclohexylene, 1,4-cyclohexylene, etc. are examples of cycloalkylene residues (=cycloalkanediyl residues).

Bicycloalkyl residues, tricycloalkyl residues, tetracycloalkyl residues and pentacycloalkyl residues preferably are $(C_6-C_{12})$-cycloalkyl residues. Like monocyclic cycloalkyl residues, polycyclic cycloalkyl residues can be unsubstituted or substituted in any desired suitable positions, for example by one or more oxo groups and/or one or more identical or different halogen atoms and/or one or more identical or different $(C_1-C_4)$-alkyl groups, for example methyl or isopropyl groups, preferably methyl groups. The free bond of a polycyclic cycloalkyl residue via which it is bonded can be located in any desired position in the molecule; the residue can thus be bonded via a bridgehead atom or via an atom in a bridge. The free bond can also be located in any desired stereochemical position, for example in an exo-position or an endo-position. Examples of bicycloalkyl residues and tricycloalkyl residues are, camphanyl, bornyl, adamantyl, such as 1-adamantyl and 2-adamantyl, caranyl, epiisobornyl, epibornyl, norbornyl and norpinanyl. An example of a pentacycloalkyl residue is the cubyl residue (pentacyclo[$4.2.0.0^{2,5}.0^{3,8}.0^{4,7}$]octyl residue).

Examples of halogen are fluorine, chlorine, bromine or iodine.

If not stated otherwise, $(C_5-C_{14})$-aryl includes heterocyclic $(C_5-C_{14})$-aryl residues (=$(C_5-C_{14})$-heteroaryl residues) in which one or more of the 5 to 14 ring carbon atoms are replaced by heteroatoms such as nitrogen, oxygen or sulfur, and carbocyclic $(C_5-C_{14})$-aryl residues. Examples of carbocyclic $(C_6-C_{14})$-aryl residues, and thus also examples of $(C_5-C_{14})$-aryl residues, are phenyl, naphthyl, biphenylyl, anthryl or fluorenyl, where 1-naphthyl, 2-naphthyl and in particular phenyl are preferred. If not stated otherwise aryl residues, for example phenyl residues, can be unsubstituted or substituted by one or more residues, for example by one, two, three, four or five identical or different residues, preferably by one, two or three residues. In particular, if not stated otherwise, aryl residues can be substituted by identical or different residues from the series consisting of $(C_1-C_8)$-alkyl, in particular $(C_1-C_4)$-alkyl, $(C_3-C_8)$-cycloalkyl, $(C_1-C_8)$-alkoxy, in particular $(C_1-C_4)$-alkoxy, halogen, such as fluorine, chlorine and bromine, nitro, amino, trifluoromethyl, hydroxyl, methylenedioxy, ethylenedioxy, cyano, hydroxycarbonyl, aminocarbonyl, $(C_1-C_4)$-alkoxycarbonyl, phenyl, phenoxy, benzyl and benzyloxy. Generally, only up to two nitro groups can occur as substituents in the compounds of the formula I according to the invention.

In monosubstituted phenyl residues, the substituent can be located in the 2-position, the 3-position or the 4-position, the 3- and the 4-position being preferred. If phenyl is disubstituted the substituents can be in the 2,3-position, 2,4-position, 2,5-position, 2,6-position, 3,4-position or 3,5-position. In trisubstituted phenyl residues, the substituents can be in the 2,3,4-position, 2,3,5-position, 2,3,6-position, 2,4,5-position, 2,4,6-position or 3,4,5-position.

Beside carbocyclic systems, $(C_5-C_{14})$-aryl residues can also be monocyclic or polycyclic aromatic ring systems in which 1, 2, 3, 4 or 5 ring carbon atoms of the corresponding cyclic hydrocarbon system are replaced by heteroatoms, provided that the resulting aromatic heterocyclic system is stable. Thus, in such heterocyclic $(C_5-C_{14})$-aryl residues 5 to 14 ring atoms are present of which 1 to 5 ring atoms are heteroatoms and the others are carbon atoms. The heteroatoms can be identical or different. In particular the heteroatoms are selected from the series consisting of nitrogen, oxygen and sulfur. Examples of such heterocyclic $(C_5-C_{14})$-aryl residues (=$(C_5-C_{14})$-heteroaryl residues), and thus also examples of $(C_5-C_{14})$-aryl residues, are pyrrolyl, furyl, thienyl, imidazolyl, pyrazolyl, oxazolyl, isoxazolyl, thiazolyl, isothiazolyl, tetrazolyl, pyridyl such as 2-pyridyl or 3-pyridyl or 4-pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl, or benzo-fused, cyclopenta-, cyclohexa- or cyclohepta-fused derivatives of these residues. If not stated otherwise, the above statements relating to substituents on carbocylic aryl residues also apply to heteroaryl residues. Thus, heteroaryl residues can be unsubstituted or substituted in all desired positions by one or more substituents, for example one, two, three, four or five identical or different substituents, in particular those substituents which are listed above as substituents on carbocyclic aryl systems.

In the series of heteroaryl residues, monocyclic or bicyclic aromatic ring systems are preferred which contain 1, 2 or 3 identical or different ring heteroatoms, in particular 1 or 2 ring heteroatoms, from the series consisting of N, O and S, and which are unsubstituted or substituted by 1, 2 or 3 identical or different substituents from the series consisting of ($C_1$–$C_6$)-alkyl, ($C_1$–$C_6$)-alkoxy, fluorine, chlorine, nitro, amino, trifluoromethyl, hydroxyl, ($C_1$–$C_4$)-alkoxycarbonyl, phenyl, phenoxy, benzyloxy and benzyl. Particularly preferred heteroaryl residues are monocyclic or bicyclic aromatic 5- to 10-membered ring systems which contain 1 to 3 heteroatoms, in particular 1 or 2 heteroatoms, from the series consisting of N, O and S and which are unsubstituted or substituted by 1 to 2 identical or different substituents from the series consisting of ($C_1$–$C_4$)-alkyl, ($C_1$–$C_4$)-alkoxy, phenyl, phenoxy, benzyl and benzyloxy.

Optically active carbon atoms present in the compounds of the formula I can independently of one another have R configuration or S configuration. The compounds of the formula I can be present in the form of pure enantiomers or pure diastereomers or in the form of mixtures of enantiomers, for example in the form of racemates, or in the form of mixtures of diastereomers. The present invention relates to pure enantiomers and mixtures of enantiomers as well as to pure diastereomers and mixtures of diastereomers. The invention comprises mixtures of two or of more than two stereoisomers of the formula I, and it comprises all ratios of stereoisomers in the mixtures. With respect to ring systems like cyclocalkyl residues or cycloalkylene residues, in which the relative position of substituents or free bonds, for example the relative position of the two free bonds in cycloalkylene residues, is usually designated as trans position or cis position, respectively, the present invention comprises the cis isomers as well as the trans isomers, and also mixtures of cis isomers and trans isomers in all ratios. Double bonds in the compounds of the formula I can independently have E configuration or Z configuration. With respect to each occurrence of E/Z isomerism, the present invention comprises both pure E isomers and pure Z isomers and E/Z mixtures in all ratios. The invention also comprises all tautomeric forms of the compounds of the formula I, for example beside the form shown in the formula I also the form in which the acylguanidine unit is present as a —CO—N=C(NHR$^1$)—NR$^2$R$^6$ group and all other forms which differ from one another by different positions of mobile hydrogen atoms. If desired, individual stereoisomers can be obtained from mixtures of stereoisomers by customary separation techniques well known to one skilled in the art, or they can be obtained by using stereochemical uniform starting materials or employing stereoselective syntheses. Diastereomers including cis/trans isomers and E/Z isomers can be separated into the individual isomers, for example, by chromatography. Racemates can be separated into the two enantiomers by customary resolution methods like, for example, chromatography on chiral phases or crystallization of derivatives.

Physiologically tolerable salts of the compounds of formula I are, in particular, nontoxic, physiologically utilizable salts or pharmaceutically utilizable salts. Such salts of compounds of the formula I which contain acidic groups, for example carboxyl group, are, for example, alkali metal salts or alkaline earth metal salts such as, for example, sodium salts, potassium salts, magnesium salts and calcium salts, and also salts with physiologically tolerable quaternary ammonium ions as well as acid addition salts with ammonia and with physiologically tolerable organic amines such as, for example, triethylamine, ethanolamine or tris-(2-hydroxyethyl)amine. Compounds of the formula I which contain basic groups form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds of the formula I which contain a basic group as well as an acidic group, for example the guanidino group and a carboxyl group, can be present as zwitterions (betaines) which are likewise a subject of the present invention.

The physiologically tolerable anion Q$^-$, which is contained in the compounds of the formula I when R$^4$ is an alkyl residue that carries a positively charged ammonium group as substituent, is in particular a monovalent anion or an equivalent of a polyvalent anion of a nontoxic, physiologically utilizable or pharmaceutically utilizable inorganic or organic acid, for example the anion or an anion equivalent of one of the abovementioned acids suitable for the formation of acid addition salts. Q$^-$ can thus be, for example, an anion (or an anion equivalent) like chloride, sulfate, phosphate, acetate, citrate, benzoate, maleate, fumarate, tartrate, methanesulfonate or p-toluenesulfonate.

Salts of compounds of the formula I can be obtained by customary methods known to one skilled in the art, for example by combining a compound of the formula I with an inorganic or organic acid or base, respectively, in a solvent or dispersant, or from other salts by cation exchange or anion exchange. The present invention also includes all salts of the compounds of the formula I which, because of low physiologically tolerability, are not directly suitable for use in pharmaceuticals, but are suitable, for example, as intermediates for carrying out chemical modifications of the compounds of the formula I, or which are suitable as starting materials for the preparation of physiologically tolerable salts.

The present invention moreover includes all solvates of compounds of the formula I, for example hydrates or adducts with alcohols, and also derivatives of the compounds of the formula I, for example esters, prodrugs and other physiologically tolerable derivatives, as well as active metabolites of the compounds of the formula I. The invention relates in particular to prodrugs of the compounds of the formula I, which can be converted into compounds of the formula I under physiological conditions. Suitable prodrugs the compounds of the formula I, i.e. chemically modified derivatives of the compounds of the formula I which have properties that are improved in a desired manner, are known to those skilled in the art. More detailed information relating to prodrugs is found, for example, in Fleisher et al., Advanced Drug Delivery Reviews 19 (1996) 115–130; Design of Prodrugs, H. Bundgaard, Ed., Elsevier, 1985; H. Bundgaard, Drugs of the Future 16 (1991) 443; Saulnier et al., Bioorg. Med. Chem. Lett. 4 (1994) 1985; Safadi et al., Pharmaceutical Res. 10 (1993) 1350. Suitable prodrugs for the compounds of the formula I are especially ester prodrugs of carboxylic acid groups, in particular of the COOH group which is present when R$^4$ in the group COOR$^4$ is hydrogen, and also acyl prodrugs and carbamate prodrugs of acylatable nitrogen-containing groups such as amino groups and in particular the guanidino group. In the acyl prodrugs or carbamate prodrugs once or more than once, for example once or twice, a hydrogen atom bonded to a nitrogen atom in a group like an amino group or a guanidino group is replaced with an acyl group or a carbamate group. Suitable acyl groups and carbamate groups for the acyl prodrugs and carbamate prodrugs are, for example, the groups $R^{10}$—CO— and $R^{11}O$—CO—, in which $R^{10}$ is hydrogen, $(C_1-C_{18})$-alkyl, $(C_3-C_{12})$-cycloalkyl, $(C_3-C_{12})$-cycloalkyl-$(C_1-C_8)$-alkyl-, $(C_5-C_{14})$-aryl, in which 1 to 5 carbon atoms can be replaced by heteroatoms such as N, O, S, or $(C_5-C_{14})$-aryl-$(C_1-C_8)$-alkyl-, in which 1 to 5 carbon atoms in the aryl moiety can be replaced by heteroatoms such as N, O, S, and $R^{11}$ has the meanings indicated for $R^{10}$ with the exception of hydrogen.

The group A in the formula I can be, for example, the residue —$(CH_2)_p$— in which p is 1, 2, 3, 4, 5, 6, 7, 8 or 9 and which can be unsubstituted or substituted as indicated above for the group A in general. Examples of a $(C_3-C_7)$-cycloalkylene residue representing the group A are 1,2-cyclopropylene or 1,2-cyclobutylene which can be unstibstituted or substituted as indicated above. If an alkylene or cycloalkylene residue representing A is substituted it is preferably substituted by one or two substituents. The group A preferably is a saturated or unsaturated bivalent $(C_1-C_5)$-alkylene residue, for example the residue —$(CH_2)_p$— in which p is 1, 2, 3, 4 or 5, or is a bivalent $(C_3-C_5)$-cycloalkylene residue wherein the alkylene residue and the cycloalkylene residue each is unsubstituted or is substituted by one or two residues from the series consisting of halogen, $(C_1-C_6)$-alkyl, $(C_1-C_6)$-alkoxy, $(C_5-C_{14})$-aryl, $(C_6-C_{14})$-aryl-$(C_1-C_6)$-alkyl-, $(C_5-C_{14})$-heteroaryl, $(C_5-C_{14})$-heteroaryl-$(C_1-C_6)$-alkyl-, $(C_3-C_{12})$-cycloalkyl, $(C_3-C_{12})$-cycloalkyl-$(C_1-C_6)$-alkyl- and oxo. Particularly preferably A is a saturated or unsaturated bivalent $(C_1-C_3)$-alkylene residue, for example the residue —$(CH_2)_p$— in which p is 1, 2, or 3, or is a bivalent $(C_3-C_5)$-cycloalkylene residue wherein the alkylene residue and the cycloalkylene residue each is unsubstituted or substituted by one or two residues from the series consisting of flourine, chlorine, bromine, $(C_1-C_6)$-alkyl, $(C_1-C_6)$-alkoxy, $(C_6-C_{14})$-aryl, $(C_6-C_{14})$-aryl-$(C_1-C_6)$-alkyl-, $(C_5-C_{14})$-heteroaryl, $(C_5-C_{14})$-heteroaryl-$(C_1-C_5)$-alkyl-, $(C_3-C_{12})$-cycloalkyl, $(C_3-C_{12})$-cycloalkyl-$(C_1-C_6)$-alkyl- and oxo. Especially preferably A is an unsubstituted $(C_1-C_3)$-alkylene group, for example a —$CH_2$— group-, a —$CH_2$—$CH_2$— group, or a —$CH_2$—$CH_2$—$CH_2$— group.

Unless stated otherwise, aryl residues and heteroaryl residues present in the group B can be unsubstituted or substituted by one or more substituents as indicated above in detail for aryl residues and heteroaryl residues in general. If a $(C_1-C_{14})$-alkyl group present in the group B is substituted by one or more halogen atoms it is preferably substituted by 1, 2, 3, 4, 5, 6 or 7 identical or different halogen atoms, particularly preferably by 1, 2, 3, 4 or 5 halogen atoms. The halogen atoms can be present in any desired positions. Preferred halogen atoms occurring as substituents in a $(C_1-C_{14})$-alkyl group are fluorine and chlorine. The group B preferably is hydrogen, —NH—CO—$OR^5$, —NH—$SO_2$—$(C_1-C_{14})$-alkyl wherein the alkyl group is unsubstituted or substituted by one or more halogen atoms, —NH—$SO_2$—$(C_6-C_{14})$-aryl or —NH—$SO_2$—$(C_5-C_{14})$-heteroaryl. If D is $(C_6-C_{14})$-aryl, $(C_5-C_{14})$-heteroaryl or $R^5$ the group B particularly preferably is hydrogen. If D is hydrogen the group B particularly preferably is a group different from hydrogen. If D is hydrogen the group B especially preferably is a group selected from the series consisting of —NH—CO—$OR^5$, —NH—$SO_2$-$(C_1-C_{14})$-alkyl wherein the alkyl group is unsubstituted or substituted by one or more halogen atoms, —NH—$SO_2$—$(C_6-C_{14})$-aryl and —NH—$SO_2$—$(C_5-C_{14})$-heteroaryl.

Unless stated otherwise, aryl residues and heteroaryl residues present in the group D can be unsubstituted or substituted by one or more substituents as indicated above in detail for aryl residues and heteroaryl residues in general. If B is hydrogen the group D preferably is $(C_6-C_{14})$-aryl, $(C_5-C_{14})$-heteroaryl or $R^5$, particularly preferably $(C_6-C_{14})$-aryl or $(C_5-C_{14})$-heteroaryl. If B is a group different from hydrogen the group D preferably is hydrogen.

If alkyl residues representing $R^1$ and/or $R^2$ are substituted they are preferably independently of one another monosubstituted or disubstituted, in particular monosubstituted, by identical or different residues $R^3$. If the residues $R^1$ and $R^2$ together are an alkylene residue which is substituted, the alkylene residue preferably is substituted by 1, 2, 3 or 4 identical or different substituents. An example of an alkylene residue representing $R^1$ and $R^2$ together is the residue —$(CH_2)_p$—, in which p is 2, 3, 4, 5, 6, 7, 8 or 9 and which can be unsubstituted or substituted as indicated above.

If the two residues $R^1$ and $R^2$ together represent a bivalent saturated or unsaturated $(C_2-C_9)$-alkylene residue these two residues together with the two nitrogen atoms to which they are bonded and the central carbon atom of the guanidino group to which these two nitrogen atoms are bonded, form a monocyclic 1,3-diazaheterocycle which is bonded to the nitrogen atom in the group A—CO—NH via its 2-position. The 1,3-diazaheterocycle can be substituted as indicated above in the $(C_2-C_9)$-alkylene residue and/or on the guanidino nitrogen atom which forms part of the diazaheterocycle. Examples of residues of such 1,3-diazaheterocycles are the 2-imidazolyl residue, the 4,5-dihydro-2-imidazolyl residue, the 1,4,5,6-tetrahydro-2-pyrimidinyl residue or the 4,5,6,7-tetrahydro-1H-1,3-diazepin-2-yl residue. If a 5- to 7-membered ring is fused to a carbon—carbon bond in the $(C_2-C_9)$-alkylene residue, then the two residues $R^1$ and $R^2$ together with the two nitrogen atoms to which they are bonded and the central carbon atom of the guanidino group to which these two nitrogen atoms are bonded, form a bicyclic 1,3-diazaheterocycle which is bonded to the nitrogen atom in the group A—CO—NH and which can be substituted as indicated. The fused (or condensed) 5- to 7-membered ring can be saturated or mono-unsaturated or di-unsaturated or aromatic. Thus, for example, a cyclopentane ring, a cyclohexane ring, a cyclohexene ring, a cyclohexadiene ring, a cycloheptane ring or a benzene ring can be condensed to a carbon—carbon bond in the $(C_2-C_9)$-alkylene residue. Examples of residues of such bicyclic heterocycles which can represent the group —C(=$NR^1$)—$NR^2R^6$ and which thus can be bonded to the nitrogen atom in the group A—CO—NH are the 1,3a,4,5,6,6a-hexahydro-1,3-diazapentalen-2-yl residue, the 1H-2-benzimidazolyl residue, the 3a,4,5,6,7,7a-hexahydro-1H-benzimidazol-2-yl residue, the 4,5,6,7-tetrahydro-1H-benzimidazol-2-yl residue, the 4,7-dihydro-1H-benzimidazol-2-yl residue or the 1H-imidazo[4,5-b]pyridin-2-yl residue. If a carbocyclic or heterocyclic ring fused to a carbon—carbon bond in an alkylene group representing $R^1$ and $R^2$ together is substituted it preferably is substituted by one or two identical or different residues $R^3$.

The residues $R^1$ and $R^2$ preferably are hydrogen or together are a saturated or unsaturated, in particular a saturated, bivalent $(C_2-C_5)$-alkylene residue, in particular a $(C_2-C_4)$-alkylene residue, especially a $(C_2-C_3)$-alkylene residue, which is unsubstituted or is substituted by one or two identical or different residues, in particular by one residue, from the series consisting of halogen, $(C_1-C_6)$-alkyl, $(C_1-C_6)$-alkoxy, $(C_6-C_{14})$-aryl, $(C_6-C_{14})$-aryl-$(C_1-C_6)$-alkyl-, $(C_5-C_{14})$-heteroaryl, $(C_5-C_{14})$-heteroaryl- ($C_1$–$C_6$)-alkyl-, ($C_3$–$C_{12}$)-cycloalkyl, ($C_3$–$C_{12}$)-cycloalkyl-($C_1$–$C_5$)-alkyl- and oxo, where a 5- to 7-membered saturated or unsaturated ring which is unsubstituted or is substituted by $R^3$, in particular by one or two residues $R^3$, and which is a carbocyclic ring or a heterocyclic ring containing one or two ring nitrogen atoms, can be fused to a carbon—carbon bond in the alkylene residue. The residues $R^1$ and $R^2$ particularly preferably are hydrogen or together are the residue —(CH$_2$)$_p$—, in which p is 2, 3, 4 or 5, preferably 2, 3 or 4, particularly preferably 2 or 3, and which is unsubstituted or is substituted by one to four, in particular one or two, identical or different residues from the series consisting of halogen, ($C_1$–$C_6$)-alkyl, ($C_1$–$C_6$)-alkoxy, ($C_6$–$C_{14}$)-aryl, ($C_6$–$C_{14}$)-aryl-($C_1$–$C_6$)-alkyl-, ($C_5$–$C_{14}$)-heteroaryl, ($C_5$–$C_{14}$)-heteroaryl-($C_1$–$C_6$)-alkyl-, ($C_3$–$C_{12}$)-cycloalkyl, ($C_3$–$C_{12}$)-cycloalkyl-($C_1$–$C_6$)-alkyl- and oxo, where a 5- to 7-membered saturated or unsaturated ring which is unsubstituted or is substituted by $R^3$, in particular by one or two residues $R^3$, and which is a carbocyclic ring or a heterocyclic ring containing one or two ring nitrogen atoms, can be fused to a carbon—carbon bond in the residue —(CH$_2$)$_p$—. Especially preferably $R^1$ and $R^2$ both are hydrogen or $R^1$ und $R^2$ together are a 1,2-ethylene residue —CH$_2$—CH$_2$— or a 1,3-propylene residue —CH$_2$—CH$_2$—CH$_2$—.

$R^3$ preferably is ($C_1$–$C_4$)-alkyl or ($C_1$–$C_4$)-alkoxy.

$R^4$ preferably is hydrogen or is unsubstituted or substituted ($C_1$–$C_6$)-alkyl, particularly preferably hydrogen or ($C_1$–$C_6$)-alkyl which is unsubstituted or substituted by a residue from the series consisting of ($C_1$–$C_4$)-alkoxy, ($C_1$–$C_4$)-alkyl-S(O)$_2$— and —NR$^7$R$^{7a}$, where $R^7$ and $R^{7a}$ independently of one another are hydrogen or ($C_1$–$C_4$)-alkyl. $R^4$ more particularly preferably is hydrogen or is unsubstituted or substituted ($C_1$–$C_4$)-alkyl, especially preferably hydrogen or ($C_1$–$C_4$)-alkyl which is unsubstituted or substituted by a residue from the series consisting of ($C_1$–$C_4$)-alkoxy, ($C_1$–$C_4$)-alkyl-S(O)$_2$— and —NR$^7$R$^{7a}$, where $R^7$ and $R^{7a}$ independently of one another are hydrogen or ($C_1$–$C_4$)-alkyl, moreover preferably hydrogen or unsubstituted ($C_1$–$C_4$)-alkyl.

If in an ($C_6$–$C_{14}$)-aryl-($C_1$–$C_6$)-alkyl- residue or ($C_5$–$C_{14}$)-heteroaryl-($C_1$–$C_5$)-alkyl- residue representing $R^5$ the aryl residue or the heteroaryl residue is substituted it is preferably substituted by one, two or three identical or different substituents $R^3$. A group $R^5$ that is not bonded to a SO$_2$ group preferably is ($C_1$–$C_{10}$)-alkyl, ($C_3$–$C_{12}$)-cycloalkyl, ($C_3$–$C_{12}$)-cycloalkyl-($C_1$–$C_6$)-alkyl- or a residue of the formula II

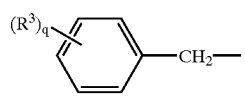

II in which the residues $R^3$ can be identical or different and can be located in any desired positions of the phenyl residue, and wherein q is 0, 1 or 2, preferably 0 or 1, particularly preferably 0. Such a group $R^5$ particularly preferably is ($C_1$–$C_7$)-alkyl, ($C_6$–$C_{12}$)-cycloalkyl, ($C_6$–$C_{12}$)cycloalkyl-($C_1$–$C_4$)-alkyl or the residue of the formula II in which q is 0 or 1. Very particularly preferably such a group $R^5$ is ($C_9$–$C_{12}$)-cycloalkyl-($C_1$–$C_3$)-alkyl, for example adamantylmethyl-, or the residue of the formula II in which q is 0 or 1. In this latter case the group $R^5$ is an unsubstituted benzyl residue or a benzyl residue which is monosubstituted in the ortho-position, meta-position or para-position by a residue $R^3$. A group $R^5$ that is bonded to a SO$_2$ group, i.e. a group $R^5$ in the group —NH—SO$_2$—$R^5$, preferably is ($C_1$–$C_{14}$)-alkyl wherein the alkyl group is unsubstituted or substituted by one or more halogen atoms, particularly preferably ($C_1$–$C_{10}$)-alkyl, more particularly preferably ($C_1$–$C_7$)-alkyl, wherein the alkyl groups are unsubstituted or substituted by one or more halogen atoms.

$R^6$ preferably is hydrogen or ($C_1$–$C_6$)-alkyl-O—CO—, particularly preferably hydrogen or ($C_1$–$C_4$)-alkyl-O—CO—, especially preferably hydrogen.

Preferred compounds of the formula I are those compounds in which one or more of the residues defined in the general definition of the compounds of formula I have preferred meanings, all possible combinations of preferred meanings or of specific denotations expressly being a subject of the present invention. Preferred compounds are, for example, compounds of the formula I in which $R^1$ and $R^2$ both are hydrogen or $R^1$ und $R^2$ together are one of the bivalent residues 1,2-ethylene and 1,3-propylene, and $R^6$ is hydrogen. Also with respect to all preferred compounds all their stereoisomeric forms and mixtures thereof in all ratios, and their physiologically tolerable salts and their prodrugs are comprised by the present invention.

Particularly preferred compounds of the formula I are those compounds in which

A is a saturated or unsaturated bivalent ($C_1$–$C_5$)-alkylene residue or a bivalent ($C_3$–$C_5$)-cycloalkylene residue, wherein the alkylene residue and the cycloalkylene residue each is unsubstituted or is substituted by one or two residues from the series consisting of halogen, ($C_1$–$C_6$)-alkyl, ($C_1$–$C_6$)-alkoxy, ($C_6$–$C_{14}$)-aryl, ($C_6$–$C_{14}$)-aryl-($C_1$–$C_6$)-alkyl-, ($C_5$–$C_{14}$)-heteroaryl, ($C_5$–$C_{14}$)-heteroaryl-($C_1$–$C_6$)-alkyl-, ($C_3$–$C_{12}$)-cycloalkyl, ($C_3$–$C_{12}$)-cycloalkyl-($C_1$–$C_6$)-alkyl- and oxo;

B is hydrogen, —NH—CO—OR$^5$, —NH—SO$_2$—($C_1$–$C_{14}$)-alkyl wherein the alkyl group is unsubstituted or substituted by one or more halogen atoms, —NH—SO$_2$—($C_6$–$C_{14}$)-aryl or —NH—SO$_2$—($C_5$–$C_{14}$)-heteroaryl;

D is hydrogen, ($C_6$–$C_{14}$)-aryl, ($C_5$–$C_{14}$)-heteroaryl or $R^5$;

$R^1$ and $R^2$ are hydrogen or together are a saturated or unsaturated bivalent ($C_2$–$C_5$)-alkylene residue which is unsubstituted or is substituted by one or two residues from the series consisting of halogen, ($C_1$–$C_6$)-alkyl, ($C_1$–$C_6$)-alkoxy, ($C_6$–$C_{14}$)-aryl, ($C_6$–$C_{14}$)-aryl-($C_1$–$C_6$)-alkyl-, ($C_5$–$C_{14}$)-heteroaryl, ($C_5$–$C_{14}$)-heteroaryl-($C_1$–$C_6$)-alkyl-, ($C_3$–$C_{12}$)-cycloalkyl, ($C_3$–$C_{12}$)-cycloalkyl-($C_1$–$C_6$)-alkyl- and oxo, where a 5- to 7-membered saturated or unsaturated ring which is unsubstituted or substituted by $R^3$ and which is a carbocyclic ring or a heterocyclic ring containing one or two ring nitrogen atoms, can be fused to a carbon—carbon bond in the ($C_2$–$C_5$)-alkylene residue;

$R^3$ is ($C_1$–$C_4$)-alkyl or ($C_1$–$C_4$)-alkoxy;

$R^4$ is hydrogen or ($C_1$–$C_6$)-alkyl which is unsubstituted or is substituted by a residue from the series consisting of ($C_1$–$C_4$)-alkoxy, ($C_1$–$C_4$)-alkyl-S(O)$_2$— and —NR$^7$R$^{7a}$, where $R^7$ and $R^{7a}$ independently of one another are hydrogen or ($C_1$–$C_4$)-alkyl;

$R^5$ is ($C_1$–$C_{10}$)-alkyl, ($C_3$–$C_{12}$)-cycloalkyl, ($C_3$–$C_{12}$)-cycloalkyl-($C_1$–$C_6$)-alkyl- or a residue of the formula II

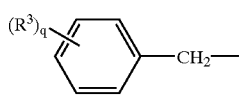

in which q is 0 or 1 and the residue $R^3$ can be located in any desired position of the phenyl residue;

$R^6$ is hydrogen or $(C_1–C_6)$-alkyl-O—CO—;

in all their stereoisomeric forms and mixtures thereof in all ratios, and their physiologically tolerable salts and their prodrugs.

Very particularly preferred compounds of the formula I are those compounds in which A is a saturated or unsaturated bivalent $(C_1–C_3)$-alkylene residue or a bivalent $(C_3–C_5)$-cycloalkylene residue, wherein the alkylene residue and the cycloalkylene residue each is unsubstituted or is substituted by one or two residues from the series consisting of flourine, chlorine, bromine, $(C_1–C_6)$-alkyl, $(C_1–C_6)$-alkoxy, $(C_5–C_{14})$-aryl, $(C_6–C_{14})$-aryl-$(C_1–C_6)$-alkyl-, $(C_5–C_{14})$-heteroaryl, $(C_5–C_{14})$-heteroaryl-$(C_1–C_6)$-alkyl-, $(C_3–C_{12})$-cycloalkyl, $(C_3–C_{12})$-cycloalkyl-$(C_1–C_6)$-alkyl- and oxo;

B is hydrogen, —NH—CO—OR$^5$, —NH—SO$_2$—$(C_1–C_{14})$-alkyl wherein the alkyl group is unsubstituted or substituted by one or more halogen atoms, —NH—SO$_2$—$(C_6–C_{14})$-aryl or —NH—SO$_2$—$(C_5–C_{14})$-heteroaryl;

D is hydrogen, $(C_6–C_{14})$-aryl or $(C_5–C_{14})$-heteroaryl;

$R^1$ and $R^2$ are hydrogen or together are a saturated or unsaturated bivalent $(C_2–C_4)$-alkylene residue which is unsubstituted or is substituted by one or two residues from the series consisting of halogen, $(C_1–C_5)$-alkyl, $(C_1–C_6)$-alkoxy, $(C_6–C_{14})$-aryl, $(C_6–C_{14})$-aryl-$(C_1–C_6)$-alkyl-, $(C_5–C_{14})$-heteroaryl, $(C_5–C_{14})$-heteroaryl-$(C_1–C_6)$-alkyl-, $(C_3–C_{12})$-cycloalkyl, $(C_3–C_{12})$-cyclocalkyl-$(C_1–C_5)$-alkyl- and oxo, where a 5- to 7-membered saturated or unsaturated ring which is unsubstituted or is substituted by $R^3$ and which is a carbocyclic ring or a heterocyclic ring containing one or two ring nitrogen atoms, can be fused to a carbon—carbon bond in the $(C_2–C_4)$-alkylene residue;

$R^3$ is $(C_1–C_4)$-alkyl or $(C_1–C_4)$-alkoxy;

$R^4$ is hydrogen or $(C_1–C_6)$-alkyl;

$R^5$ is $(C_1–C_7)$-alkyl, $(C_6–C_{12})$-cycloalkyl, $(C_6–C_{12})$-cycloalkyl-$(C_1–C_4)$-alkyl- or a residue of the formula II

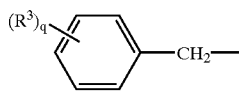

in which q is 0 or 1 and the residue $R^3$ can be located in any desired position of the phenyl residue;

$R^6$ is hydrogen or $(C_1–C_4)$-alkyl-O—CO—;

in all their stereoisomeric forms and mixtures thereof in all ratios, and their physiologically tolerable salts and their prodrugs.

Especially preferred compounds of the formula I are those in which

A is a saturated or unsaturated bivalent $(C_1–C_3)$-alkylene residue or a bivalent $(C_3–C_5)$-cycloalkylene residue, wherein the alkylene residue and the cycloalkylene residue is unsubstituted;

B is hydrogen, —NH—CO—OR$^5$, —NH—SO$_2$—$(C_1–C_{14})$-alkyl wherein the alkyl group is unsubstituted or substituted by one or more halogen atoms, —NH—SO$_2$—$(C_6–C_{14})$-aryl or —NH—SO$_2$—$(C_5–C_{14})$-heteroaryl;

D is hydrogen, $(C_6–C_{14})$-aryl or $(C_5–C_{14})$-heteroaryl;

$R^1$ and $R^2$ are hydrogen or together are a saturated or unsaturated bivalent $(C_2–C_3)$-alkylene residue which is unsubstituted, where a 5- to 7-membered saturated or unsaturated ring which is unsubstituted or is substituted by $R^3$ and which is a carbocyclic ring or a heterocyclic ring containing one or two ring nitrogen atoms, can be fused to a carbon—carbon bond in the $(C_2–C_3)$-alkylene residue;

$R^3$ is $(C_1–C_4)$-alkyl or $(C_1–C_4)$-alkoxy;

$R^4$ is hydrogen or $(C_1–C_4)$-alkyl;

$R^5$ is $(C_1–C_7)$-alkyl, $(C_5–C_{12})$-cycloalkyl, $(C_6–C_{12})$-cycloalkyl-$(C_1–C_4)$-alkyl- or a residue of the formula II

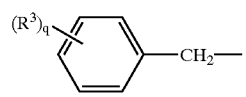

in which q is 0 or 1 and the residue $R^3$ can be located in any desired position of the phenyl residue;

$R^6$ is hydrogen or $(C_1–C_4)$-alkyl-O—CO—;

in all their stereoisomeric forms and mixtures thereof in all ratios, and their physiologically tolerable salts and their prodrugs.

If the carbon atom to which the group B is bonded is chiral preferred compounds of the formula I are furthermore those in which the carbon atom to which the group B is bonded, has S configuration, in particular in compounds of the formula I in which D is hydrogen. Further, if the carbon atom to which the group D is bonded is chiral preferred compounds of the formula I are those in which the carbon atom to which the group D is bonded, has S configuration, in particular in compounds of the formula I in which B is hydrogen.

A specific group of compounds of the present invention is formed by the compounds of the formula I in which A is a saturated or unsaturated bivalent $(C_1–C_9)$-alkylene residue or a bivalent $(C_3–C_7)$-cycloalkylene residue, wherein the alkylene residue and the cycloalkylene residue each is unsubstituted or is substituted by one or more residues from the series consisting of halogen, $(C_1–C_6)$-alkyl, $(C_1–C_6)$-alkoxy, $(C_6–C_{14})$-aryl, $(C_6–C_{14})$-aryl-$(C_1–C_6)$-alkyl-, $(C_5–C_{14})$-heteroaryl, $(C_5–C_{14})$-heteroaryl-$(C_1–C_6)$-alkyl-, $(C_3–C_{12})$-cycloalkyl, $(C_3–C_{12})$-cycloalkyl-$(C_1–C_6)$-alkyl- and oxo;

B is hydrogen, —NH—CO—OR$^5$, —NH—SO$_2$—R$^5$, —NH—SO$_2$—$(C_6–C_{14})$-aryl, —NH—SO$_2$—$(C_5–C_{14})$-heteroaryl, —NH—CO—R$^5$, —NH—CO—$(C_6–C_{14})$-aryl, —NH—CO—$(C_5–C_{14})$-heteroaryl, —NH—CO—NH—R$^5$, —NH—CO—NH—$(C_6–C_{14})$-aryl, —NH—CO—NH—$(C_5–C_{14})$-heteroaryl, —NH—SO$_2$—NH—R$^5$, —NH—SO$_2$—NH—$(C_6–C_{14})$-aryl or —NH—SO$_2$—NH—$(C_5–C_{14})$-heteroaryl;

D is hydrogen, $(C_6–C_{14})$-aryl, $(C_5–C_{14})$-heteroaryl or R$^5$;

$R^1$ and $R^2$ independently of one another are hydrogen or $(C_1–C_6)$-alkyl which is unsubstituted or substituted by one or more residues $R^3$, or $R^1$ and $R^2$ together are a saturated or unsaturated bivalent $(C_2-C_9)$-alkylene residue which is unsubstituted or is substituted by one or more residues from the series consisting of halogen, $(C_1-C_6)$-alkyl, $(C_1-C_5)$-alkoxy, $(C_6-C_{14})$-aryl, $(C_6-C_{14})$-aryl-$(C_1-C_6)$-alkyl-, $(C_5-C_{14})$-heteroaryl, $(C_5-C_{14})$-heteroaryl-$(C_1-C_6)$-alkyl-, $(C_3-C_{12})$-cycloalkyl, $(C_3-C_{12})$-cycloalkyl-$(C_1-C_6)$-alkyl- and oxo, where a 5- to 7-membered saturated or unsaturated ring which is unsubstituted or is substituted by one or more residues $R^3$ and which is a carbocyclic ring or a heterocyclic ring containing one or two ring nitrogen atoms, can be fused to a carbon—carbon bond in the $(C_2-C_9)$-alkylene residue;

$R^3$ is $(C_1-C_8)$-alkyl, $(C_1-C_8)$-alkoxy, $(C_5-C_{14})$-aryl, $(C_5-C_{14})$-aryl-$(C_1-C_4)$-alkyl-, halogen, trifluoromethyl, hydroxyl, nitro or amino;

$R^4$ is hydrogen, $(C_1-C_6)$-alkyl-CO—O—$(C_1-C_4)$-alkyl- or $(C_1-C_6)$-alkyl, which is unsubstituted or is substituted by a residue from the series consisting of hydroxyl, $(C_1-C_4)$-alkoxy, $(C_1-C_4)$-alkyl-S(O)$_2$—, —NR$^7$R$^{7a}$ and —NR$^7$R$^{7a}$R$^{7b}$Q$^-$, where R$^7$, R$^{7a}$ and R$^{7b}$ independently of one another are hydrogen, $(C_1-C_6)$-alkyl, $(C_5-C_{14})$-aryl or $(C_5-C_{14})$-aryl-$(C_1-C_6)$-alkyl- and Q$^-$ is a physiologically tolerable anion, or $R^4$ is one of the residues

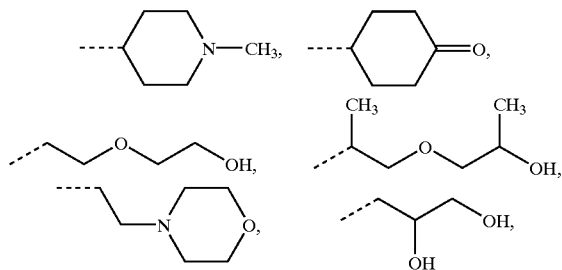

in which the bonds via which the residues are bonded, are indicated by dashed lines;

$R^5$ is $(C_1-C_{14})$-alkyl , $(C_3-C_{12})$-cycloalkyl, $(C_3-C_{12})$-cycloalkyl-$(C_1-C_5)$-alkyl-, $(C_5-C_{14})$-aryl-$(C_1-C_6)$-alkyl- or $(C_5-C_{14})$-heteroaryl-$(C_1-C_6)$-alkyl-, where the aryl residue and the heteroaryl residue is unsubstituted or is substituted by one or more residues $R^3$;

$R^6$ is hydrogen, $(C_1-C_5)$-alkyl-O—CO—, hydroxyl, $(C_1-C_5)$-alkyl-O—CO—O— or nitro;

in all their stereoisomeric forms and mixtures thereof in all ratios, and their physiologically tolerable salts and their prodrugs.

The present invention also relates to processes for the preparation of the compounds of the formula I. The compounds can generally be prepared, for example in the course of a convergent synthesis, by linkage of two or more fragments which can be derived retrosynthetically from the formula I. In the preparation of the compounds of the formula I it can generally be advantageous or necessary in the course of the synthesis to introduce functional groups which could lead to undesired reactions or side reactions in the respective synthesis step, in the form of precursor groups which are later converted into the desired functional groups, or to temporarily block functional groups by using a protective group strategy suitably adapted to the specific synthesis problem. Such strategies are well known to one skilled in the art (cf. Greene and Wuts, Protective Groups in Organic Synthesis, Wiley, 1991).

Thus the compounds of the formula I can be prepared, for example, by linking in a manner known per se a carboxylic acid or carboxylic acid derivative of the formula III

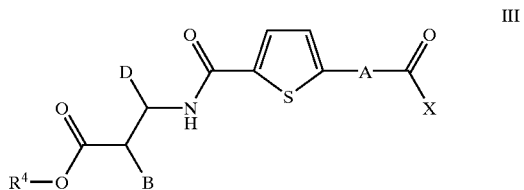

in which $R^4$, A, B and D are defined as indicated above for the formula I, or in which functional groups can also be present in the form of precursor groups which are later converted into the groups present in the compounds of the formula I, or functional groups can be present in protected form, and in which X is a nucleophilically substitutable leaving group examples of which are given below, with a guanidine or guanidine derivative of the formula IV

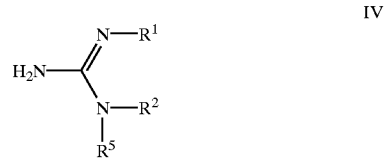

in which $R^1$, $R^2$ and $R^6$ are defined as indicated for the formula I, or in which functional groups can also be present in the form of precursor groups which are later converted into the groups present in the compounds of the formula I, or functional groups can be present in protected form. For example, in the compounds of the formula III the group $R^4$ can, besides the denotations given for the formula I, also denote a carboxylic acid protecting group which after condensation of the compounds of the formulae III and IV is removed in order to obtain a compound of the formula I in which $R^4$ is hydrogen. Similarly, for example, the condensation reaction can be performed with a compound of the formula III in which B denotes a group NH-PG wherein PG is an amino protecting group which is removed after the condensation reaction to yield a free amino group NH$_2$ which is then converted into the desired target group, for example by sulfonylation or conversion into a carbamate group, amide group or urea group by standard procedures. Examples of precursor groups are nitro groups which can later be converted into amino groups, or cyano groups which can be converted into aminomethyl groups or carboxylic acid groups.

Beside the free guanidines of the formula IV also guanidinium salts can be employed in the reaction with the compounds of the formula III. In this case the free guanidines can be prepared from their salts in situ or in a separate step by means of a base according to standard procedures.

The group COX in the formula III preferably is the carboxylic acid group COOH or an activated carboxylic acid derivative, X can be, for example, hydroxyl; halogen, in particular chlorine or bromine; alkoxy, preferably methoxy or ethoxy; aryloxy, for example phenoxy or pentafluorophenoxy; phenylthio; methylthio; 2-pyridylthio; or a residue of a nitrogen heterocycle bonded via a nitrogen atom, in particular a residue of an azole, such as, for example, 1-imidazolyl. Furthermore, an activated acid derivative can be a mixed anhydride, i.e. X can be, for example, ((C$_1$-C$_4$)-alkyl)-O—CO—O— or tolylsulfonyloxy.

If X is hydroxyl, i.e. if the guanidine of the formula IV is reacted with a carboxylic acid, then the carboxylic acid is expediently first activated. The activation can be carried out, for example, with dicyclohexylcarbodiimide (DCCI) or with O-((cyano(ethoxycarbonyl)methylen)amino)-1,1,3,3-tetramethyluronium tetrafluoroborate (TOTU; König et al., Proc. 21st Europ. Peptide Symp. 1990 (Eds. Giralt, Andreu), Escom, Leiden 1991, p. 143) or with other activating reagents customary in peptide chemistry.

The reaction of an activated carboxylic acid derivative of the formula III with the guanidine (derivative) of the formula IV is preferably carried out in a manner known per se in a protic or aprotic polar, but inert, organic solvent. In this case, methanol, isopropanol, tert-butanol, dimethylformamide or tetrahydrofuran at temperatures from 0° C. up to the boiling point of these solvents have proven suitable, for example, in the reaction of a methyl ester (X=methoxy) or of an ethyl ester (X=ethoxy) with a guanidine (derivative). The reactions of compounds of the type COX with salt-free guanidines are advantageously carried out in aprotic inert solvents such as dimethylformamide, tetrahydrofuran, dimethoxyethane or dioxane, if appropriate with addition of a base such as, for example, potassium tert-butoxide or sodium methoxide. However, water can also be used as a solvent in the reaction of compounds of the formula III with guanidines, for example when using a base such as sodium hydroxide. If X is chlorine, the reaction is advantageously carried out with addition of an acid scavenger, for example with addition of an added base or in the presence of excess guanidine (derivative), for binding the resulting hydrohalic acid. The reaction mixture is worked up and, if desired, the reaction product is then purified by the customary processes familiar to one skilled in the art.

Protective groups optionally still present in the products obtained from the starting compounds of the formulae III and IV are then removed by standard processes. For example, tert-butyl ester groups can be converted into the carboxylic acid groups by treatment with trifluoroacetic acid, benzyl groups can be removed by hydrogenation, or fluorenylmethoxycarbonyl groups can be removed by secondary amines. If desired, further reactions, for example acylation reactions, can be carried out by standard processes, as well as a conversion into a physiologically tolerable salt or into a prodrug can be carried out by known processes.

The starting components of the formulae III and IV, which are linked to give the acylguanidine derivatives of the formula I, are commercially available or can be prepared by or analogously to processes described in the literature. Synthetic ways for preparing starting components of the formula III are exemplarily illustrated in scheme 1. The present invention, however, is not restricted to the depicted syntheses or starting components. It does not cause any problems to one

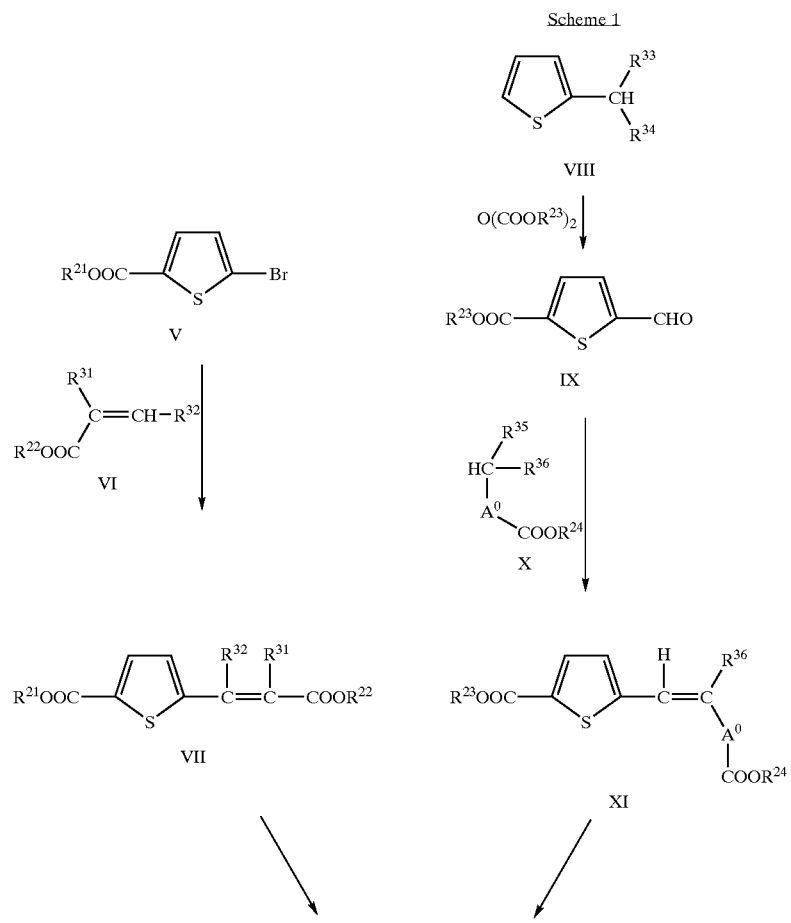

Scheme 1

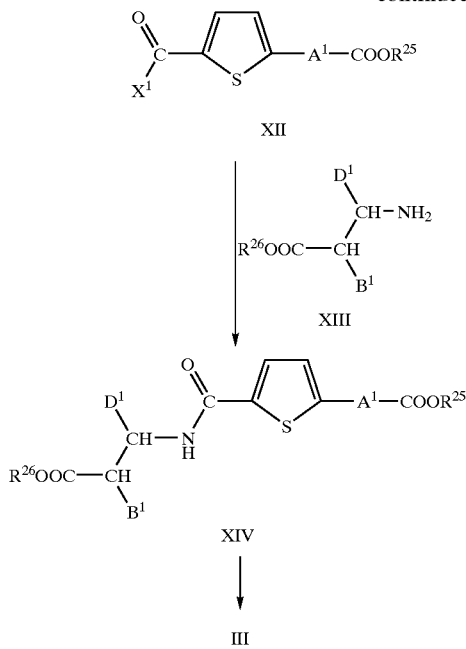

skilled in the art to carry out the modifications of the syntheses shown which are necessary for the preparation of other compounds according to the invention. The synthesis of a compound of the formula III may, for example, start from a bromothiophene carboxylic acid or a derivative thereof of the formula V in which $R^{21}$ is, for example, hydrogen, $(C_1-C_4)$-alkyl, benzyl or a carboxylic acid protective group. A compound of the formula V can be coupled in the presence of a transition metal catalyst like, for example, a palladium complex with an α,β-unsaturated carboxylic acid derivative of the formula VI in which $R^{22}$ can be, for example, $(C_1-C_4)$-alkyl. $R^{31}$ and $R^{32}$ in formula VI, as well as in formula VII, can be hydrogen or carbon substituents that can be present in an alkylene group representing the group A in the compounds of formula I, or $R^{31}$ and $R^{32}$ together with the two carbon atoms to which they are bonded may form a cycloalkene ring, where functional groups present in $R^{31}$ and $R^{32}$ may also be present in protected form or in the form or precursor groups. Such a coupling reaction yielding a compound of formula VII, just as any other reaction mentioned in this section on the synthesis of compounds of the formula III, can be performed under conditions comprehensively described in the literature and/or in the experimental section. The resulting compound of the formula VII may already be a compound which without further modifications is reacted with an amino acid derivative of the formula XIII (see below) to give a compound of the formula XIV. However, before being reacted with a compound of the formula XIII a compound of the formula VII may also first be modified in one or more reaction steps in the groups $COOR^{21}$ and/or $COOR^{22}$ and/or in the $CR^{31}$=$CR^{32}$ moiety. For example, an ester group may be cleaved to give a carboxylic acid group and/or an activated carboxylic acid derivative may be prepared. The double bond in the $CR^{31}$=$CR^{32}$ moiety may, for example, be modified by catalytic hydrogenation to give a single bond, or by cyclopropanation with a carbene transferring reagent like an diazoalkane, a sulfur ylide or methylene iodide to give a cyclopropane derivative. After such modifications a compound of the formula XII is obtained in which the group $X^1$ is a nucleophilically substitutable leaving group. All the above statements with respect to the group X in the compounds of the formula III also apply to the group $X^1$ in the compounds of formula XII. The group $R^{25}$ is, for example, hydrogen, $(C_1-C_4)$-alkyl, benzyl or a carboxylic acid protective group. The group $A^1$ is defined as the group A in the compounds of the formula I or can also be a precursor group of the group A which can be transformed into the desired group A, or can also contain functional groups in protected form.

In a further synthetic route to compounds of the formula III a protected thiophene aldehyde of the formula VIII is employed as starting material. In formula VIII the groups $R^{33}$ and $R^{34}$ are, for example, alkoxy groups or dialkylamino groups, or the groups $R^{33}$ and $R^{34}$ together with the CH group to which they are bonded form a heterocyclic ring like, for example, a 1,3-dioxolane ring, a perhydro-1,3-dioxane ring, an N,N'-dialkylimidazolidine ring, an N-alkyl-1,3-oxazolidine ring or an N-alkyl-perhydro-1,3-oxazine ring which all may carry further substituents like alkyl groups, and wherein alkyl preferably denotes $(C_1-C_4)$-alkyl. After metallation with, for example, an organolithium compound like butyl lithium a compound of the formula VIII is reacted with a reagent introducing a carboxylic acid function, for example with a dicarbonic acid ester of the formula $O(COOR^{23})_2$ or a chloroformic acid ester of the formula in $ClCOOR^{23}$ wherein $R^{23}$ is, for example, $(C_1-C_4)$-alkyl or benzyl. In the primary reaction product the protected aldehyde group is deprotected to give a formylthiophene carboxylic acid derivative of formula IX in which, as in formula XI, the group $R^{23}$ is for example $(C_1-C_4)$-alkyl or benzyl. The aldehyde function in the compound of formula IX is then converted into an olefine under standard olefination conditions by reacting it with a suitable compound of the formula X. In addition, aldehydes of formula IX are also suitable starting materials for the preparation of compounds of the present invention in which A in the formula I is $C_1$-alkylene, i.e. a methylene group. For the preparation of these latter compounds the aldehyde function may, for example, be reduced to a hydroxymethyl group which after activation by mesylation or tosylation can be converted into a $CH_2$—CN group wherein the CN group can then be converted into a carboxylic acid or an ester thereof.

Examples of compounds of the formula X are malonic acid derivatives or phosphorus compounds like phosphonic acid esters or phosphonium salts. In the case of malonic acid derivatives the group $R^{35}$ in the formula X is a carboxylic acid group (or a salt thereof), $R^{36}$ is hydrogen, $A^0$ is a direct bond, and $R^{24}$ is, for example, $(C_1-C_4)$-alkyl. In the case of phosphorus compounds the group $R^{35}$ in the formula X may be a positively charged phosphonium salt group having a negative counterion, for example a triphenylphosphonium group with chloride, bromide or iodide as counterion, or the group $R^{35}$ may be a phosphonic acid ester group, for example a diethyl phosphonate group of the formula $(C_2H_5O)_2P(O)$—. In phosphorus compounds of the formula X the group $R^{36}$ is hydrogen or a carbon substituent that can be present in an alkylene group representing the group A in the compounds of the formula I, and the group $R^{24}$ is, for example, $(C_1-C_4)$-alkyl or benzyl. The group $A^0$ in phosphorus compounds of the formula X is a direct bond or a saturated or unsaturated bivalent $(C_1-C_7)$-alkylene residue. The definitions given for the compounds of the formulae IX and X also apply to the compounds of the formula XI.

Condensations of the compounds of formulae IX and X can be carried out under standard conditions. If the compound of formula X is a malonic acid ester salt, the components may be reacted, for example, in the presence of pyridine and piperidine. If the compound of the formula X is a phosphonium salt or a phosphonic acid ester, according to the customary procedure applied in Wittig reactions or Wittig Horner reactions, it usually is first deprotonated with a suitable base like, for example, sodium hydride, lithium diisopropylamide, potassium tert-butoxide or another alkali metal alcoholate to give a phosphorane or a metal salt of the phosphonic acid ester, respectively, and is then reacted with the aldehyde of formula IX. The resulting compound of formula XI, like the compounds of formula VII, may already be a compound which without further modifications is reacted with an amino acid derivative of the formula XIII to give a compound of the formula XIV. However, before being reacted with a compound of the formula XIII a compound of the formula XI may also first be modified in one or more reaction steps in the groups $COOR^{23}$ and/or $COOR^{24}$ and/or in the CH=$CR^{36}$ moiety and/or in the group $A^0$, for example by cleaving ester groups and/or preparing an activated carboxylic acid derivative and/or modifying double bonds by catalytic hydrogenation or by cyclopropanation. After such modifications a compound of the formula XII is obtained in which the residues have the meanings already indicated above.

In the compounds of formula XIII, as well as in the compounds of formula XIV, the residues $R^{26}$, $B^1$ and $D_1$ have the meanings of the residues $R^4$, B and D, respectively, in the compounds of formula I, but functional groups within them can also be present in the form of precursor groups or can be present in protected form. If in the desired target compound of formula I the group B denotes hydrogen, the corresponding starting compound of the formula XIII is a 3-aminopropionic acid derivative. If in the target compound the group B is a substituted amino group, the corresponding starting compound of the formula XIII is a 2,3-diaminopropionic acid derivative. If $X^1$ in the formula XII is hydroxyl the condensation of the $NH_2$ group in the propionic acid derivative of formula XIII with the $COX^1$ group in the compound of formula XII can be carried similarly as described above for the condensation of the compounds of formulae III and IV, for example in the presence of TOTU or another customary activating agent for carboxylic acids, and the above statements then correspondingly also apply to the present reaction. The resulting condensation product of the formula XIV may already be a compound which without further modifications is reacted with a guanidine (derivative) of the formula IV. In such a case the compound of the formula XIV also is a compound of the formula III. However, before being reacted with a compound of the formula IV, a compound of the formula XIV may also first be modified in one or more reaction steps in the groups $COOR^{25}$ and/or $COOR^{26}$ and/or in further groups like the groups $A^1$ or $B^1$. For example, an ester group representing the group $COOR^{25}$ may be cleaved to give a carboxylic acid group, and/or an activated carboxylic acid derivative may be prepared. A double bond present in the group $A^1$ may, for example, be modified by catalytic hydrogenation to give a single bond, or by cyclopropanation as outlined above. After such modifications a compound of the formula III is obtained.

Thus, if in a compound of formula XIV obtained from the syntheses described above the group $COOR^{25}$ is an activated carboxylic acid derivative, the compound of formula XIV can be reacted directly with a compound of formula IV. If in a compound of formula XIV the group $COOR^{25}$ is an ester group and it is not intended to react this compound directly with a compound of formula IV, the ester group can also first be cleaved under standard conditions to give the corresponding carboxylic acid which is then reacted with a guanidine of formula IV after in situ activation, for example with TOTU or DCCI, or after conversion into an activated carboxylic acid derivative. If, as activated acid derivative, it is intended to prepare, for example, the carboxylic acid chloride (formula III, X=Cl), this can be carried out by using, for example, thionyl chloride. If it is intended to prepare, for example, the methyl ester (X=methoxy) from the carboxylic acid, this can be carried out by treating with gaseous hydrogen chloride in methanol. Other activated acid derivatives can be prepared in a manner known per se from the carboxylic acid chlorides or directly from the carboxylic acids on which they are based (X=OH), for example the imidazolides (X=1-imidazolyl) by treating the acids with carbonyldiimidazole (cf. Staab, Angew. Chem. Int. Ed. Engl. 1, 351–367 (1962)), or for example the mixed anhydrides by reaction with chloroformic acid esters such as ethyl chloroformate or with tosyl chloride in the presence of an amine such as triethylamine in an inert solvent. A number of suitable methods for the preparation of activated carboxylic acid derivatives are indicated with details of source literature in J. March, Advanced Organic Chemistry, Third Edition, John Wiley & Sons, 1985, p. 350.

The compounds of the formula I are valuable pharmaceutical active compounds which are suitable, for example, for the therapy and prophylaxis of bone disorders, tumor diseases or cardiovascular disorders. The compounds of the formula I and their physiologically tolerable salts and their prodrugs can be administered to animals, preferably to mammals, and in particular to humans as pharmaceuticals for therapy or prophylaxis. They can be administered on their own, in mixtures with one another or in the form of pharmaceutical preparations (or pharmaceutical compositions) which permit enteral or parenteral administration and which, as active ingredient, contain an efficacious dose of at least one compound of the formula I and/or its physiologically tolerable salts and/or its prodrugs in addition to customary pharmaceutically acceptable carriers and/or additives.

The present invention therefore also relates to the compounds of the formula I and/or their physiologically tolerable salts and/or their prodrugs for use as pharmaceuticals, to the use of the compounds of the formula I and/or their physiologically tolerable salts and/or their prodrugs for the production of pharmaceuticals for the therapy and prophylaxis of the diseases mentioned above or below, for example for the therapy and prophylaxis of bone disorders, and also to the use of the compounds of the formula I and/or their physiologically tolerable salts and/or their prodrugs in the therapy and prophylaxis of these diseases. The present invention furthermore relates to pharmaceutical preparations which contain an efficacious dose of at least one compound of the formula I and/or its physiologically tolerable salts and/or its prodrugs in addition to a customary pharmaceutically acceptable carrier.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or transdermally, for example in the form of ointments, solutions or tinctures, or in other ways, for example in the form of aerosols or nasal sprays.

The pharmaceutical preparations according to the invention are prepared in a manner known per se, pharmaceutically inert inorganic and/or organic carriers or excipients being used in addition to the compound(s) of the formula I and/or its (their) physiologically tolerable salts and/or its (their) prodrugs. For the production of pills, tablets, coated tablets and hard gelatin capsules, it is possible to use, for example, lactose, corn starch or derivatives thereof, talc, stearic acid or its salts, etc. Carriers for soft gelatin capsules and suppositories are, for example, fats, waxes, semisolid and liquid polyols, natural or hardened oils, etc. Suitable carriers for the production of solutions, for example injection solutions, or of emulsions or syrups are, for example, water, alcohols, glycerol, polyols, sucrose, invert sugar, glucose, vegetable oils, etc. Suitable carriers for microcapsules, implants or rods are, for example, copolymers of glycolic acid and lactic acid.

In addition to the active ingredients and carriers, the pharmaceutical preparations can additionally contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula and/or their physiologically tolerable salts and/or their prodrugs. Furthermore, in addition to at least one compound of the formula I and/or its physiologically tolerable salts and/or its prodrugs, they can also contain one or more other therapeutically or prophylactically active ingredients.

The pharmaceutical preparations normally contain approximately 0.5 to 90% by weight of the compounds of the formula I and/or their physiologically tolerable salts and/or their prodrugs. The amount of active ingredient of the formula I and/or its physiologically tolerable salts and/or its prodrugs in a pharmaceutical preparation normally is 0.2 to 1000 mg, preferably 1 to 200 mg.

The compounds of the formula I are antagonists of the vitronectin receptor and have, for example, the ability to inhibit the binding of osteoclasts to the bone surface and thereby inhibit bone resorption by osteoclasts. The action of the compounds of the formula I can be demonstrated, for example, in an assay in which the inhibition of the binding of vitronectin to cells which contain the vitronectin receptor is determined. Details of such an assay are given below. As vitronectin receptor antagonists, the compounds of the formula I and their physiologically tolerable salts and their prodrugs are generally suitable for the therapy and prophylaxis of diseases which are based on the interaction between vitronectin receptors and their ligands in cell cell interaction processes or cell matrix interaction processes, or which can be influenced by an inhibition of interactions of this type, or for the prevention, alleviation or cure of which an inhibition of interactions of this type is desired. As explained at the beginning, such interactions play a part, for example, in bone resorption, in angiogenesis or in the proliferation of cells of the vascular smooth musculature. The compounds of the formula I and their physiologically tolerable salts and their prodrugs are therefore suitable, for example, for the alleviation or cure of diseases which are caused at least partially by an undesired extent of bone resorption, angiogenesis or proliferation of cells of the vascular smooth musculature.

Bone diseases for whose treatment and prevention the compounds of the formula I according to the invention can be employed are especially osteoporosis, hypercalcemia, osteopenia, for example caused by metastases, dental disorders, hyperparathyroidism, periarticular erosions in rheumatoid arthritis and Paget's disease. In addition, the compounds of the formula I can be used for the alleviation, avoidance or therapy of bone disorders which are caused by a glucocorticoid, steroid or corticosteroid therapy or by a lack of sex hormone(s). All these disorders are characterized by bone loss which is based on the inequilibrium between bone formation and bone destruction and which can favorably be influenced by the inhibition of bone resorption by osteoclasts.

The compounds of the formula I and/or their physiologically tolerable salts and/or their prodrugs can also favorably be used as inhibitor of bone resorption, for example in the therapy or prophylaxis of osteoporosis, in combination with conventional osteoporosis treatments, for example in combination with agents like bisphosphonates, estrogens, estrogen/progesterone, estrogen agonists/antagonists, calcitonin, vitamin D analogues, parathyroid hormone, growth hormone secretagogues, or sodium fluoride. Administration of the compounds of the formula I and/or their physiologically tolerable salts and/or their prodrugs and of other active ingredients effective in the treatment or prophylaxis of osteoporosis like those listed before can take place simultaneously or sequentially, in any order, and jointly or separately. For use in such a combination treatment or prophylaxis the compounds of the formula I and/or their physiologically tolerable salts and/or their prodrugs and one or more other active ingredients like those listed before can together be present in a single pharmaceutical preparation, for example tablets, capsules or granules, or can be present in two or more separate pharmaceutical preparations which can be contained in a single package or in two or more separate packages. The use of the compounds of the formula I and/or their physiologically tolerable salts and/or their prodrugs in such a combination therapy or prophylaxis and their use in the production of pharmaceuticals for such a combination therapy or prophylaxis are also subjects of the present invention. The invention furthermore relates to pharmaceutical preparations which comprise efficacious amounts of at least one compound of the formula I and/or its physiologically tolerable salts and/or its prodrugs together with at least one other active ingredient effective in the treatment or prophylaxis of osteoporosis or in the inhibition of bone resorption like those listed before, together with a customary pharmaceutically acceptable carrier. The above explanations on pharmaceutical preparations correspondingly apply to such pharmaceutical combination preparations.

In addition to the use as inhibitors of bone resorption by osteoclasts, the compounds of the formula I and their physiologically tolerable salts and their prodrugs can be used, for example, as inhibitors of tumor growth and tumor metastasis, as antiinflammatories, for the therapy or prophylaxis of cardiovascular disorders such as arteriosclerosis or restenosis, or for the therapy or prophylaxis of nephropathies or retinopathies such as, for example, diabetic retinopathy. As inhibitors of tumor growth or tumor metastasis the compounds of the formula I and/or their physiologically tolerable salts and/or their prodrugs can also favorably be used in combination with conventional cancer therapy. Examples of conventional cancer therapy are given in Bertino (Editor), Encyclopedia of Cancer, Academic Press, 1997 which is incorporated herein by reference. All the above statements relating to the use of the compounds of formula I in combination with conventional osteoporosis therapy like, for example, possible modes of administration and pharmaceutical combination preparations, correspondingly apply to the use of the compounds of formula I in combination with conventional cancer therapy.

When using the compounds of the formula I, the dose can vary within wide limits. As is known to those skilled in the art, the dose is to be suited to the individual conditions in each individual case. It depends, for example, on the compound employed, on the nature and severity of the disease to be treated and on whether an acute or chronic condition is treated or whether prophylaxis is carried out. In the case of oral administration, for achieving effective results in an adult weighing about 75 kg the daily dose generally is about 0.01 to 100 mg/kg, preferably about 0.1 to 50 mg/kg, in particular about 0.1 to 10 mg/kg (in each case in mg per kg of body weight). Also in the case of intravenous administration the daily dose generally is about 0.01 to 100 mg/kg, preferably about 0.05 to 10 mg/kg (in each case in mg per kg of body weight). The daily dose can be divided, in particular in the case of administration of relatively large amounts, into several, for example 2, 3 or 4, part administrations. If appropriate, depending on individual behavior, it may be necessary to deviate upwards or downwards from the daily dose indicated.

Beside their use as active ingredients in pharmaceutical preparations, the compounds of the formula I can also be used as vehicles or carriers of other active ingredients in order to transport the other active ingredient specifically to the site of action (=drug targeting; see, for example, Targeted Drug Delivery, R. C. Juliano, Handbook of Experimental Pharmacology, Vol. 100, Ed. Born, G. V. R. et al., Springer Verlag). The active ingredients to be transported are in particular those which can be used for the treatment of the abovementioned diseases.

The compounds of the formula I and their salts can furthermore be employed for diagnostic purposes, for example in in vitro diagnoses, and as auxiliaries in biochemical investigations when blocking of the vitronectin receptor or influencing of cell cell or cell matrix interactions is desired for diagnostic or research purposes. They can furthermore be used as intermediates for the preparation of other compounds, in particular of other pharmaceutical active compounds, which are obtainable from the compounds of the formula I, for example by chemical modification or introduction of residues or functional groups.

EXAMPLES

The products were identified via mass spectra and/or NMR spectra. When in the final synthesis step of a compound an acid such as trifluoroacetic acid or acetic acid was used, for example when trifluoroacetic acid was employed to remove a tert-butyl group or when a compound was purified by chromatography using an eluent which contained such an acid, and when the compound was then freeze-dried, in some cases, depending on how the freeze-drying was carried out, the compound still contained the acid that had been used, and was obtained partially or completely in the form of a salt of the acid used, for example in the form of the acetic acid salt or trifluoroacetic acid salt.

Example 1

(2S)-2-Benzyloxycarbonylamino-3-(5-(3-guanidino-3-oxo-propyl)-thiophene-2-carbonyl)-amino)-propionic Acid

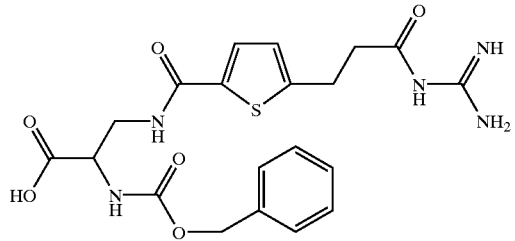

a) 5-(2-Methoxycarbonyl-vinyl)-thiophene-2-carboxylic Acid 12.8 g (62 mmol) of 5-bromo-thiophene-2-carboxylic acid were dissolved in 200 ml of acetonitrile together with 160 ml of triethylamine. To this solution were added 36 ml (approx. 0.4 mol) of methyl acrylate and 1.3 g (1.5 mmol) of (1,1'-bis(diphenylphosphino)ferrocene) dichloropalladium(II) (1:1 complex with dichloromethane; Aldrich). The mixture was heated in a glass tube in an autoclave under a nitrogen atmosphere for 20 hours at 85° C. After cooling, the suspension was filtered. The clear dark solution was evaporated in a hood, the dry residue was dissolved in water and the solution obtained was extracted twice with ethyl acetate. The organic phases were discarded. The aqueous phase was cautiously acidified with small portions of citric acid and then extracted thrice with 200 ml each of ethyl acetate. The combined extracts were dried with anhydrous magnesium sulfate and, after filtration, evaporated to yield 11.2 g of raw material. HPLC analysis of the product exhibited 2% of the educt 5-bromo-thiophene-2-carboxylic acid, 15% of the dehalogenation product 2-thiophene carboxylic acid and 82% of the title compound. After recrystallisation from water/isopropanol (700 ml water/35 ml isopropanol) and drying 8.9 g of colourless crystals of the title compound with a melting point of 156° C. and a purity of >97% (HPLC) were obtained.

b) 5-(2-Methoxycarbonyl-ethyl)-thiophene-2-carboxylic Acid 2.37 g (11.18 mmol) of 5-(2-methoxycarbonyl-vinyl)-thiophene-2-carboxylic acid were dissolved in 170 ml of methanol. After addition of 500 mg of 10% palladium on charcoal (Degussa E 101 R/D 10%) the mixture was hydrogenated for 7 hours at atmospheric pressure (approx. 1 bar) and room temperature. After filtration and evaporation the yield of the title compound was 2.4 g (purity>99% (HPLC)).

Melting point: 83–85° C.

c) (2S)-2-Benzyloxycarbonylamino-3-((5-(2-methoxycarbonyl-ethyl)-thiophene-2-carbonyl)-amino)-propionic Acid tert-Butyl Ester 1.5 g (7.0 mmol) of 5-(2-methoxycarbonyl-ethyl)-thiophene-2-carboxylic acid were dissolved in 40 ml of anhydrous dimethylformamide and stirred with 2.06 g (7 mmol) of (S)-N$^\alpha$-benzyloxycarbonyl-α,β-diaminopropionic acid tert-butyl ester and 2.3 g of TOTU (O-(cyan-(ethoxycarbonyl)-methyleneamino)-1,1,3,3-tetramethyluronium-tetrafluoroborate) under a nitrogen atmosphere at room temperature. The pH of the solution was kept at 7.5 to 8.0 by adding N,N-diisopropyl-N-ethylamine. After 6 hours the dark solution was evaporated. The residue was dissolved in 85 ml of dichloromethane, the solution was extracted with 20 ml each of saturated sodium bicarbonate solution, brine and 10% aqueous citric acid and then washed twice with water. The solution was dried with anhydrous magnesium sulfate and, after filtration, evaporated. The raw material (approx. 4 g) was purified by fractionated column chromatography (silica gel 35–70 μm; heptane/ethylacetate). The fractions containing the title compound were combined and evaporated to give 2.9 g of a colourless resin.

d) (2S)-2-Benzyloxycarbonylamino-3-((5-(3-guanidino-oxo-propyl)-thiophene-2-carbonyl)-amino)-propionic Acid tert-Butyl Ester 0.272 g (0.55 mmol) of the product obtained in step c) were suspended in 30 ml of dry tetrahydrofuran. 0.168 g (2.75 mmol) of guanidine (free base) were added. The resulting suspension was heated under reflux for 2.5 hours. The solvents were removed in vacuo and the residue was dissolved in 200 ml dichloromethane. The resulting solution was washed four times with 30 ml each of water. The organic phase was then dried with dry magnesium sulfate, filtered off and evaporated. 30 mg of a resinous material were obtained which was sufficiently pure for use in the subsequent step.

Mass spectrum: m/e=518 (M+H$^+$).

e) (2S)-2-Benzyloxycarbonylamino-3-((5-(3-guanidino-3-oxo-propyl)-thiophene-2-carbonyl)-amino)-propionic Acid 30 mg of the product obtained in step d) were dissolved in 3 ml of dichloromethane. 0.3 ml of trifluoroacetic acid were added, and the mixture was stirred at room temperature. After 3.5 hours the solution was evaporated, the residue was dissolved in 2 ml of glacial acetic acid and again evaporated in vacuo. This procedure was repeated twice. Then the residue was triturated with diethyl ether to give a suspension which, after filtration, gave 6.3 mg of the title compound as a colourless amorphous solid.

Mass spectrum: m/e=462 (M+H$^+$).

Example 2

(2S)-2-Benzyloxycarbonylamino-3-((5-(2-(1,4,5 6-tetrahydropyrimidin-2-ylcarbamoyl)-ethyl)-thiophene-2-carbonyl)-amino)-propionic Acid

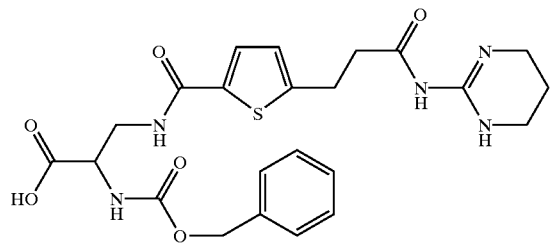

a) 1,3-Dimethyl-2-(2-thienyl)-imidazolidine 23.5 g (267 mmol) of N,N'-dimethylethylenediamine were dissolved in 300 ml of toluene and treated with 29.8 g (266 mmol) of thiophene-2-carbaldehyde. The clear mixture was refluxed for 4 hours using a Dean-Stark trap. After that time 4.9 ml of water had separated in the trap. After cooling, the solution was filtered and evaporated. The oily residue was destilled in vacuo. Yield: 45 g.

Boiling point: 65° C. (0.1 mm Hg).

b) 5-(1,3-Dimethyl-imidazolidin-2-yl)-thiophene-2-carboxylic Acid tert-Butyl Ester 7.28 g (40 mmol) of 1,3-dimethyl-2-(2-thienyl)-imidazolidine were dissolved in 50 ml of dry tetrahydrofuran. 5.12 g (40 mmol) of N,N,N',N'-tetramethylethylenediamine were added and the solution was cooled to −70° C. Then 20 ml of a 2N solution of n-butyllithium in n-hexane were added dropwise at −70° C. After stirring for further 2 hours 8.72 g (40 mmol) of di-tert-butyl pyrocarbonate, dissolved in 10 ml of dry tetrahydrofuran, were slowly added at −70° C. and stirring was continued at that temperature for further 4 h. The mixture was then allowed to warm up to room temperature overnight. The solvents were destined off and the dark red residue was dissolved in a mixture of 150 ml diethylether and 150 ml of ethyl acetate. The solution obtained was washed twice with ice water and then with brine. After drying with anhydrous magnesium sulfate and filtration, the solvents were destined off to give a dark yellow oil. The product obtained was used in the next step without further purification. Yield: 8 g.

Mass spectrum: m/e=283 (M+H$^+$).

c) 5-Formyl-thiophene-2-carboxylic Acid tert-Butyl Ester 2.54 g (9 mmol) of 5-(1,3-dimethyl-imidazolidin-2-yl)-thiophene-2-carboxylic acid tert-butyl ester wered dissolved in 15 ml of diethyl ether, and after addition of 5 ml of methyl iodide the solution was stirred overnight at room temperature. The resulting crystalline suspension was vigorously stirred for 1 hour with 100 ml water. Then 100 ml diethyl ether were added, and after separation of the phases the organic phase was dried with anhydrous magnesium sulfate. After filtration, the solvents were removed in vacuo. 1.7 g of a light brown oil were isolated which was sufficiently pure for use in the subsequent step.

Mass spectrum: m/e=213 (M+H$^+$).

d) 5-(2-Ethoxycarbonyl-vinyl)-thiophene-2-carboxylic Acid tert-Butyl Ester 1.7 g (8 mmol) of the product obtained in step c) were dissolved in 5 ml of dry tetrahydrofuran. The solution was added dropwise to a mixture of 2.24 g (10 mmol) of diethyl phosphonoacetate and 440 mg sodium hydride (55% in paraffin oil) in 30 ml of dry tetrahydrofuran. The resulting mixture was stirred at 60° C. for 3 hours. After cooling to room temperature, the mixture was poured onto water/ethyl acetate. The organic phase was separated, washed with 10% aqueous citric acid and dried with anhydrous magnesium sulfate. After filtration, the solvents were removed to give 2.6 g of raw product. This material was purified by column chromatography (silica gel; ethyl acetate/n-heptane (1/5; v/v)). The fractions containing the title compound were combined and evaporated to give 1.2 g of a clear light yellow oil.

Mass spectrum: m/e=283 (M+H$^+$).

e) 5-(2-Ethoxycarbonyl-ethyl)thiophene-2-carboxylic Acid tert-Butyl Ester 0.846 g (3 mmol) of the product obtained in step d) were dissolved in 100 ml of dry ethanol. 150 mg of 10% palladium on charcoal were added, and the suspension was hydrogenated at 50° C. and 4 bar hydrogen pressure. After filtration the solvent was removed in vacuo. 0.6 g of a colourless oil were obtained.

Mass spectrum: m/e=285 (M+H$^+$).

f) 5-(2-Ethoxycarbonyl-ethyl)-thiophene-2-carboxylic Acid 0.564 g (2 mmol) of 5-(2-ethoxycarbonyl-ethyl)-thiophene-2-carboxylic acid tert-butyl ester were dissolved in 10 ml of dichloromethane. 2.5 ml of trifluoroacetic acid were added dropwise with stirring at room temperature. Stirring was continued for 5 hours until the starting compound was no more detectable by thin layer chromatography (TLC). The solvents were evaporated in vacuo to give 0.45 g of a crystalline residue which was sufficiently pure for use in the subsequent step.

g) (2S)-2-Benzyloxycarbonylamino-3-((5-(2-ethoxycarbonyl-ethyl)-thiophene-2-carbonyl)-amino)-propionic Acid tert-Butyl Ester The product obtained in step f) was dissolved in 10 ml of anhydrous dimethylformamide. 0.588 g (2 mmol) of (S)-N$^\alpha$-benzyloxycarbonyl-α,β-diamino-propionic acid tert-butyl ester and 0.656 g (2 mmol) of TOTU were added to the solution. The pH was adjusted to approx. 8 by addition of N,N-diisopropyl-N-ethylamine and kept at this value during the reaction time by further addition of N,N-diisopropyl-N-ethylamine (approx. 5 mmol were used). After stirring at room temperature for 8 hours the starting materials were no more detectable by TLC. The solvents were removed under reduced pressure. The residue was dissolved in ethyl acetate and the solution was washed with 10% aqueous sodium bicarbonate, brine, 10% aqueous citric acid and water. After drying with anhydrous magnesium sulfate and filtration the solvent was evaporated. The residue was purified by chromatography (silica gel; ethyl acetate/heptane (1/1, v/v)). The fractions containing the title compound were pooled and evaporated in vacuo to give 320 mg of a light brownish resin.

Mass spectrum: m/e=505 (M+H$^+$), m/e=449 (M–C$_4$H$_8$+H$^+$).

h) (2S)-2-Benzyloxycarbonylamino-3-((5-(2-(1,4,5,6-tetrahydropyrimidin-2-ylcarbamoyl)-ethyl)-thiophene-2-carbonyl)-amino)-propionic Acid tert-Butyl Ester 100 mg of the product obtained in step g) were stirred with 100 mg of 2-amino-1,4,5,6-tetrahydropyrimidine in 5 ml of anhydrous dimethylformamide at room temperature until the starting material was no longer detectable (8 h). The solvent was removed under reduced pressure and the remaining residue was purified by chromatography (silica gel; ethyl acetate/methanol (1/1, v/v)). The fractions containing the title compound were pooled and evaporated in vacuo to give 50 mg of a weakly coloured resin.

Mass spectrum: m/e=558 (M+H$^+$).

i) (2S)-2-Benzyloxycarbonylamino-3-((5-(2-(1,4,5,6-tetrahydropyrimidin-2-ylcarbamoyl)-ethyl)-thiophene-2-carbonyl)-amino)-propionic Acid 50 mg of the product obtained in step h) were dissolved in 5 ml of dichloromethane, and with stirring 0.5 ml of trifluoroacetic acid were added dropwise at room temperature. After 4 hours the ester was no more detectable. The mixture was evaporated under reduced pressure, and the remaining residue was dissolved in acetic acid and again evaporated under reduced pressure. This procedure was repeated twice. Then the residue was triturated vigorously with diethyl ether. The crystals formed were isolated by suction followed by washing with diethyl ether. After drying in vacuo 30 mg of the title compound were obtained as a pale yellow powder.

Mass spectrum: m/e=502 (M+H$^+$).

Example 3

(2S)-2-Benzyloxycarbonylamino-3-((5-(2-(1,4,5,6-tetrahydropyrimidin-2-ylcarbamoyl)-cyclopropyl)-thiophene-2-carbonyl)-amino)-propionic Acid

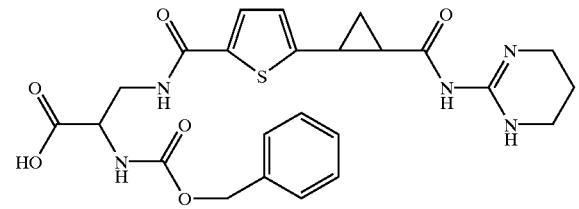

a) 3-(5-(((2S))-2-Benzyloxycarbonylamino-2-tert-butoxycarbony-ethyl)carbamyl)-2-thienyl)-acrylic Acid Methyl Ester 1.06 g (5 mmol) of 5-(2-methoxycarbonyl-vinyl)-thiophene-2-carboxylic acid were dissolved in 75 ml of anhydrous dimethylformamide. 1.47 g (5 mmol) of (S)-N$^\alpha$-benzyloxycarbonyl-α,β-diamino-propionic acid tert-butyl ester and 1.64 g (5 mmol) of TOTU were added. The mixture was stirred at room temperature under a nitrogen atmosphere. The pH of the solution was kept at 7.5–8.0 by adding N,N-diisopropyl-N-ethylamine. After 3.5 hours the dark solution was evaporated. The residue was dissolved in 85 ml of dichloromethane, extracted with 20 ml each of saturated sodium bicarbonate solution, brine, and 10% aqueous citric acid and than washed twice with water. The solution was dried with anhydrous magnesium sulfate and, after filtration, evaporated. The raw material (approx. 2.8 g) was then purified by column chromatography (silica gel 35–70 μm, heptane/ethylacetate). The fractions containing the product were combined and evaporated to give 1.47 g of the title compound as colourless crystals.

Mass spectrum: m/e=489 (M+H$^+$); 433 (M–C$_4$H$_8$+H$^+$). Melting point: 98° C.

b) 2-(5-(((2S)-2-Benzyloxycarbonylamino-2-tert-butoxycarbonyl-ethyl)carbamoyl)-2-thienyl)-cyclopropancarboxylic Acid Methyl Ester 293 mg (0.6 mmol) of the product obtained in step a) were dissolved in 10 ml of diethyl ether and 10 ml of tetrahydrofuran. 15 mg of palladium diacetate were added. To the suspension obtained an ethereal solution of diazomethane (prepared from approx. 1 g of N-nitroso-N-methyl-urea) was slowly added at 0° C. with continuous stirring. After stirring for 2 hours 0.2 ml of acetic acid were added to destroy excess diazomethane. The solvents were removed by destillation under reduced pressure, and the residue was dissolved in ethyl acetate and washed with 10% sodium hydrogencarbonate solution and then with water. The solution was dried with anhydrous magnesium sulfate and, after filtration, the solvents were removed under reduced pressure. The oily residue was chromatographed (silica gel; ethyl acetate/heptane (1/1, v/v)) to give 230 mg of a colourless oil.

Mass spectrum: m/e=503 (M+H$^+$), m/e=447 (M−C$_4$H$_8$+H$^+$).

c) (2S)-2-Benzyloxycarbonylamino-3-((5-(2-(1,4,5,6-tetrahydropyrimidin-2-ylcarbamoyl)-cyclopropyl)-thiophene-2-carbonyl)-amino)-propionic Acid tert-Butyl Ester 220 mg (0.44 mmol) of the product obtained in step b) were dissolved in 2 ml of anhydrous dimethylformamide. After addition of 100 mg 2-amino-1,4,5,6-tetrahydropyrimidine the mixture was stirred for 6 hours at room temperature. Then the solvent was removed by destillation under reduced pressure. The residue was chromatographed (silica gel; ethyl acetate/methanol (1/1, v/v)). The fractions containing the title compound were pooled and and the solvents removed. Yield: 96 mg.

Mass spectrum: m/e=570 (M+H$^+$), m/e=514 (M−C$_4$H$_8$+H$^+$).

d) (2S)-2-Benzyloxycarbonylamino-3-((5-(2-(1,4,5,6-tetrahydropyrimidin-2-ylcarbamoyl)-cyclopropyl)-thiophene-2-carbonyl)-amino)-propionic Acid 90 mg of the product obtained in step c) were dissolved in 1.5 ml of dichloromethane, and 0.5 ml of trifluoroacetic acid were added. After stirring for 4 hours at room temperature the solvents were removed in vacuo. The residue was dissolved in 3 ml of acetic acid to form a clear solution. Again solvents were removed in vacuo. This procedure was repeated once. Then the resinous residue was triturated with diethyl ether to give 55 mg of the title compound as a colourless amorphous solid.

Mass spectrum: m/e=514 (M+H$^+$).

Example 4

(2S)-2-(1-Adamantylmethoxycarbonylamino)-3-((5-(2-(1,4,5,6-tetrahydropyrimidin-2-ylcarbamoyl)-cyclopropyl)-thiophene-2-carbonyl)-amino)-propionic Acid

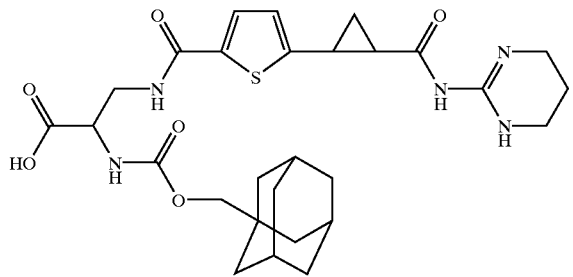

a) 3-(5-(((2S)-2-(1-Adamantylmethoxycarbonylamino)-2-tert-butoxycarbonyl-ethyl)carbamoyl)-2-thienyl)-acrylic Acid Methyl Ester The title compound was synthesized analogously to example 3, step a) from 360 mg (1.84 mmol) of 5-(2-methoxycarbonyl-vinyl)-thiophene-2-carboxylic acid and 650 mg (1.84 mmol) of (2S)-2-(1-adamantylmethoxycarbonylamino)-3-amino-propionic acid tert-butyl ester. After chromatography (silica gel; ethyl acetate/n-heptane (1/1, v/v)) 326 mg of the title compound were obtained as colourless crystals.

Melting point: 159° C.

b) 2-(5-(((2S)-2-(1-Adamantylmethoxycarbonylamino)-2-tert-butoxycarbonyl-ethyl)carbamoyl)-2-thienyl)-cyclopropancarboxylic Acid Methyl Ester The compound was synthesized analogously to example 3, step b) from 108 mg (0.2 mmol) of 3-(5-(((2S)-2-(1-adamantylmethoxycarbonylamino)-2-tert-butoxycarbonylethyl)carbamoyl)-2-thienyl)-acrylic acid methyl ester and a diazomethane solution in ether (generated from 0.5 g of N-nitroso-N-methyl-urea) in the presence of 10 mg palladium diacetate. 105 mg of a colourless oil were obtained which was sufficiently pure for use in the subsequent step.

Mass spectrum: m/e=561 (M+H$^+$).

c) (2S)-2-(1-Adamantylmethoxycarbonylamino)-3-((5-(2-(1,4,5,6-tetrahydropyrimidin-2-ylcarbamoyl)-cyclopropyl)-thiophene-2-carbonyl)-amino)-propionic Acid tert-Butyl Ester The product obtained in step b) was dissolved in 4 ml of anhydrous dimethylformamide and stirred under an argon atmosphere with 99 mg of 2-amino-1,4,5,6-tetrahydropyrimidine for 7 hours at room temperature. The solvent was removed in vacuo and the residue was chromatographed (silica gel; ethyl acetate/methanol (1/1, v/v)). The fractions containing the title compound were pooled and evaporated under reduced pressure to give 53 mg of a colourless resin.

Mass spectrum: m/e=628 (M+H$^+$).

d) (2S)-2-(1-Adamantylmethoxycarbonylamino)-3-((5-(2-(1,4,5,6-tetrahydropyrimidin-2-ylcarbamoyl)-cyclopropyl)-thiophene-2-carbonyl)-amino)-propionic Acid 48 mg of the product obtained in step c) were dissolved in 2 ml of dichloromethane and stirred for 3 hours with 1 ml of trifluoroacetic acid under an inert gas atmosphere at room temperature. The solvents were removed in vacuo, the residue was dissolved in acetic acid and the solution was again evaporated to dryness. This procedure was repeated once. The resinous residue was triturated with diethyl ether. After filtration 30 mg of the title compound were obtained as a colourless amorphous powder.

Melting point: 186° C. (decomposition) Mass spectrum: m/e=572 (M+H$^+$).

Example 5

(3S)-3-(Benzo[1,3]dioxol-5-yl)-3-((5-(2-(1,4,5,6-tetrahydropyrimidin-2-ylcarbamoyl)-ethyl)-thiophene-2-carbonyl)-amino)-propionic Acid

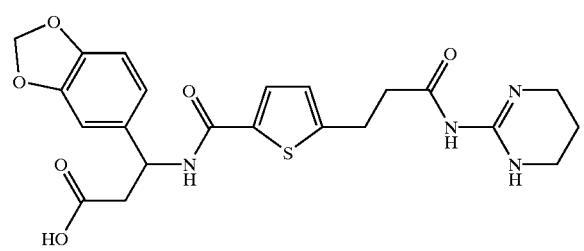

a) (3S)-3-(Benzo[1,3]dioxol-5-yl)-3-((5-(2-methoxycarbonyl-ethyl)-thiophene-2-carbonyl)-amino)-propionic Acid tert-Butyl Ester 214 mg (1 mmol) of 5-(2-methoxycarbonyl-ethyl)-thiophene-2-carboxylic acid (example 1, step b) were dissolved in 5 ml of anhydrous dimethylformamide. 265 mg (1 mmol) of (3S)-3-amino-3-(benzo[1,3]dioxol-5-yl)-propionic acid tert-butyl ester and 328 mg (1 mmol) of TOTU were added, and 3 mmol (0.51 ml) of N,N-diisopropyl-N-ethylamine were added to keep the pH of the mixture at 7.5 to 8. The reaction mixture was stirred for 4.5 hours at room temperature. Solvents were removed under reduced pressure to give a dark brown oil. The residue was dissolved in dichloromethane and washed with saturated sodium bicarbonate solution, 10% citric acid and with water. Then the organic phase was dried with anhydrous magnesium sulfate. After filtration the solvents were removed in vacuo to give 600 mg of a brownish oil which was purified by chromatography (silica gel; ethyl acetate/heptane (1/2, v/v)). 425 mg of a resin were obtained.

$^1$H NMR (D$_6$-DMSO): δ (ppm)=1.36 (s, 9H, O—C(CH$_3$)$_3$, 2.65 and 3.05 (AA'BB', 2×2H, ester-CH$_2$CH$_2$-thienyl), 2.67 (m, 2H, CHCH$_2$-tert-butyl ester), 3.61 (s, 3H, COOCH$_3$), 5.25 (m, 1H, CHCH$_2$-tert-butyl ester), 5.98 (s, 2H, OCH$_2$O), 6.82 (s, 2H) and 6.98 (s, 1H) (aromatic protons), 6.90 and 7.60 (2d, J=2 Hz, 2H, thienyl-3,4-H), 8.66 (d, J=7 Hz, 1H, amide proton).

b) (3S)-3-(Benzo[1,3]dioxol-5-yl)-3-((5-(2-(1,4,5,6-tetrahydropyrimidin-2-ylcarbamoyl)-ethyl)-thiophene-2-carbonyl)-amino)-propionic Acid tert-Butyl Ester 424 mg of the product obtained in step a) were dissolved in 4 ml of anhydrous dimethylformamide and 460 mg of 2-amino-1,4,5,6-tetrahydropyrimidine were added. The slightly yellow solution was stirred at room temperature for 4 hours. The solvents were removed in vacuo and the residue was dissolved in 30 ml of dichloromethane. The solution was washed thrice with 18 ml of water each and then dried with anhydrous magnesium sulfate. After filtration the solvents were removed in vacuo and the residue was chromatographed (silica gel, ethyl acetate/methanol (1/1, v/v)). The fractions containing the title compound were collected, and the solvents were removed in vacuo to give 345 mg of colourless crystals.

Melting point: 130° C. Mass spectrum: m/e=529 (M+H$^+$), 473 (M-C$_4$H$_8$+H$^+$).

c) (3S)-3-(Benzo[1,3]dioxol-5-yl)-3-((5-(2-(1,4,5,6-tetrahydropyrimidin-2-ylcarbamoyl)-ethyl)-thiophene-2-carbonyl)-amino)-propionic Acid 320 mg of the product obtained in step b) were dissolved in 5 ml of dichloromethane and 2 ml of trifluoroacetic acid were added. The solution was stirred at room temperature for 3 hours. Then solvents were removed in vacuo. The residue was dissolved in acetic acid and again the solvents were removed in vacuo. This procedure was repeated once. The resinous residue was then triturated with diethyl ether to give 300 mg of of the title compound as a colourless amorphous powder.

Mass spectrum: m/e=473 (M+H$^+$).

Analogously to example 5 the following compounds were synthesized.

Example 6

(3RS)-3-(3-Pyridyl)-3-((5-(2-(1,4,5,6-tetrahydropyrimidin-2-ylcarbamoyl)-ethyl)-thiophene-2-carbonyl)-amino)-propionic Acid

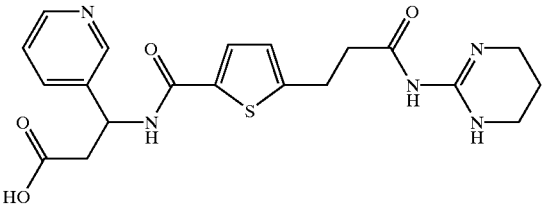

Mass spectrum: m/e=430 (M+H$^+$).

Example 7

(3RS)-3-(Benzo[1,3]dioxol-5-yl)-3-((5-(3-guanidino-3-oxo-propyl)-thiophene-2-carbonyl)-amino)-propionic Acid

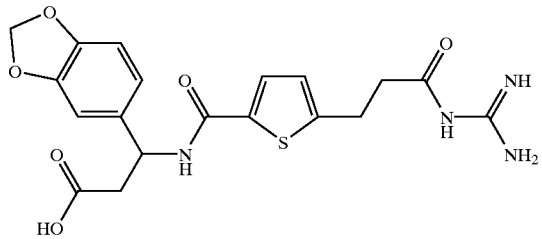

Mass spectrum: m/e=433 (M+H$^+$).

Example 8

(3RS)-3-Phenyl-3-((5-(2-(1,4,5,6-tetrahydropyrimidin-2-ylcarbamoyl)-ethyl)-thiophene-2-carbonyl)-amino)-propionic Acid

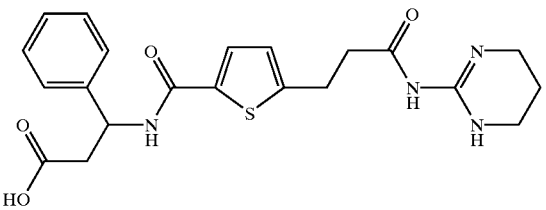

Mass spectrum: m/e=429 (M+H$^+$).

Example 9

(3RS)-3-(3,5-Difluorophenyl)-3-((5-(2-(1,4,5,6-tetrahydropyrimidin-2-ylcarbamoyl)-ethyl)-thiophene-2-carbonyl)-amino)-propionic Acid

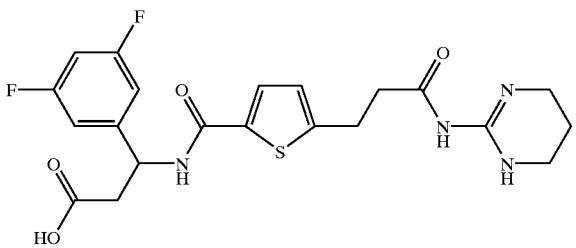

Mass spectrum: m/e=465 (M+H$^+$).

Example 10

(3S)-3-(4-Biphenylyl)-3-((5-(2-(1,4,5,6-tetrahydropyrimidin-2-ylcarbamoyl)-ethyl)-thiophene-2-carbonyl)-amino)-propionic Acid

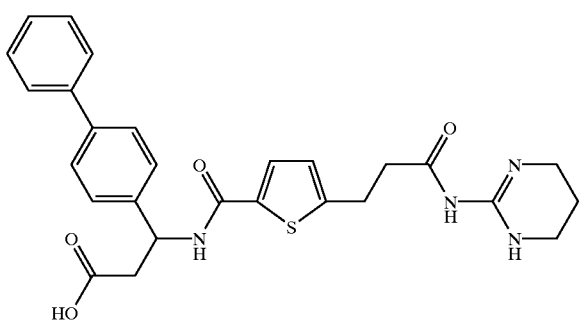

Mass spectrum: m/e=505 (M+H$^+$).

Example 11

(3RS)-3-(1-Naphthyl)-3-((5-(2-(1,4,5,6-tetrahydropyrimidin-2-ylcarbamoyl)-ethyl)-thiophene-2-carbonyl)-amino)-propionic Acid

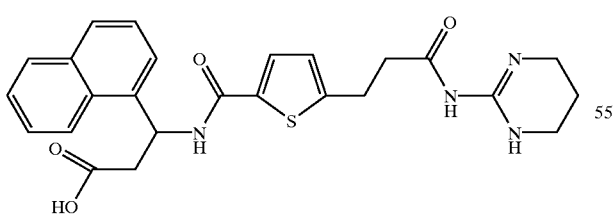

Mass spectrum: m/e=479 (M+H$^+$).

Analogously to example 5 but starting from 5-(2-methoxycarbonyl-vinyl)-thiophene-2-carboxylic acid (example 1, step a), the compounds of examples 12, 13 and 14 were synthesized.

Example 12

(3RS)-3-(Benzo[1,3]dioxol-5-yl)-3-((5-(2-(1,4,5,6-tetrahydropyrimidin-2-ylcarbamoyl)-vinyl)-thiophene-2-carbonyl)-amino)-propionic Acid

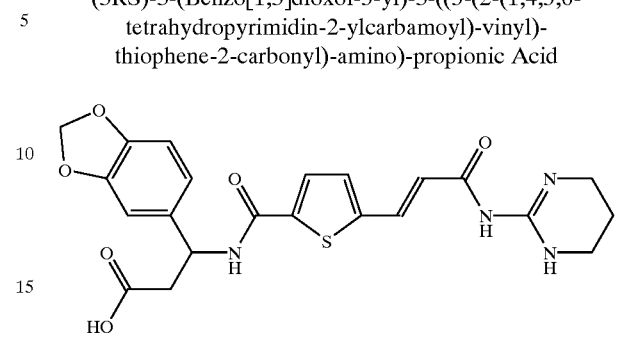

Mass spectrum: m/e=471 (M+H$^+$).

Example 13

(3RS)-3-(Benzo[1,3]dioxol-5-yl)-3-((5-(3-guanidino-3-oxo-propenyl)-thiophene-2-carbonyl)-amino)-propionic Acid

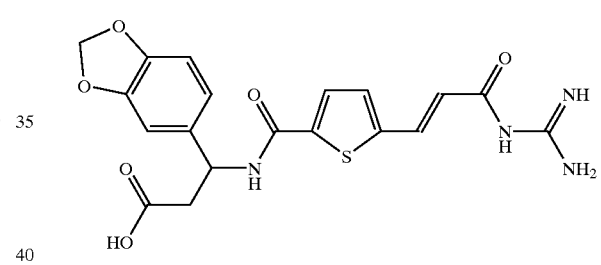

Mass spectrum: m/e=431 (M+H$^+$).

Example 14

(2S)-2-Benzyloxycarbonylamino-3-((5-(2-(1,4,5,6-tetrahydropyrimidin-2-ylcarbamoyl)-vinyl)-thiophene-2-carbonyl)-amino)-propionic Acid

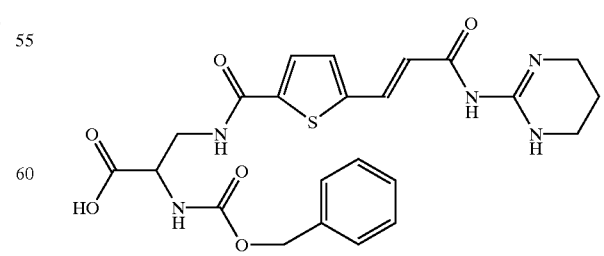

Mass spectrum: m/e=500 (M+H$^+$).

Example 15

(2S)-2-(1-Adamantylmethoxycarbonylamino)-3-((5-(2-(1,4,5,6-tetrahydropyrimidin-2-ylcarbamoyl)-ethyl)-thiophene-2-carbonyl)-amino)-propionic Acid

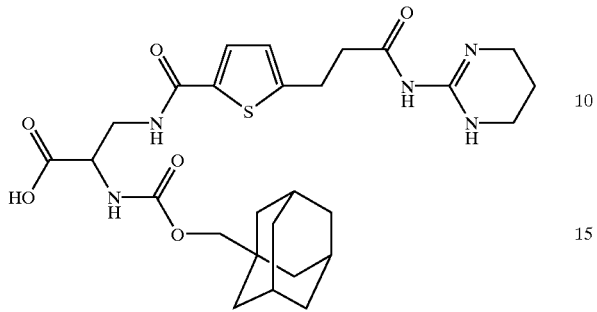

a) (2S)-2-Amino-3-((5-(2-methoxycarbonyl-ethyl)-thiophene-2-carbonyl)-amino)-propionic Acid tert-Butyl Ester Hydrochloride 6.85 g of 3-(5-(((2S)-2-benzyloxycarbonylamino-2-tert-butoxycarbonyl-ethyl)carbamoyl)-2-thienyl)-acrylic acid methyl ester (example 3, step a) were dissolved in 220 ml of methanol. 1.3 g of 10% palladium on charcoal and 2.8 ml of a 5N solution of hydrogen chloride in methanol were added and the hydrogenation was started. After 6 hours the pH was adjusted with 5N solution of hydrogen chloride in methanol to 3.5, and further 0.6 g of the catalyst were added. After 14 hours the hydrogenation was complete. The catalyst was removed by filtration. After standard work-up 4.88 g of the title compound were obtained.

Mass spectrum: m/e=357 (M+H$^+$).

b) (2S)-2-(1-Adamantylmethoxycarbonylamino)-3-((5-(2-methoxycarbonyl-ethyl)-thiophene-2-carbonyl)-amino)-propionic Acid tert-Butyl Ester 1.97 g (5 mmol) of the hydrochloride salt obtained in step a) were dissolved in a mixture of 55 ml of tetrahydrofuran, 25 ml of saturated sodium bicarbonate solution and 30 ml of water under stirring at room temperature. After addition of 1.54 g (5 mmol) of N-(1-adamantylmethoxycarbonyloxy)-succinimid stirring at room temperature was continued for 4 hours. After washing and drying, the organic solvents were removed in vacuo. The residue was chromatographed (silica gel; heptane/ethyl acetate (2/1, v/v)) to give 2.77 g of a resin.

Mass spectrum: m/e=549 (M+H$^+$).

c) (2S)-2-(1-Adamantylmethoxycarbonylamino)-3-((5-(2-(1,4,5,6-tetrahydropyrimidin-2-ylcarbamoyl)-ethyl)-thiophene-2-carbonyl)-amino)-propionic Acid tert-Butyl Ester 1.37 g (2.5 mmol) of the product obtained in step b) were dissolved in 12 ml of anhydrous dimethylformamide, and after addition of 1.24 g of 2-amino-1,4,5,6-tetrahydropyrimidine the mixture was stirred at room temperature for 5 hours. The solvent was removed in vacuo and the residue was chromatographed (silica gel; ethyl acetate/methanol (1/1; v/v)) to give 1.1 g of the title compound.

Mass spectrum: m/e=616 (M+H$^+$).

d) (2S)-2-(1-Adamantylmethoxycarbonylamino)-3-((5-(2-(1,4,5,6-tetrahydropyrimidin-2-ylcarbamoyl)-ethyl)-thiophene-2-carbonyl)-amino)-propionic Acid 117 mg (0.19 mmol) of the product obtained in step c) were dissolved in 5 ml of dichloromethane and stirred for 3 hours with 1 ml of trifluoroacetic acid under an inert gas atmosphere at room temperature. The solvents were removed in vacuo, and the residue was dissolved in acetic acid and again evaporated to dryness. This procedure was repeated once. The resinous residue was triturated with diethyl ether. After filtration 90 mg of a colourless amorphous powder were obtained.

Mass spectrum: m/e=560 (M+H$^+$).

Example 16

(2S)-2-(1-Adamantylmethoxycarbonylamino)-3-((5-(2-(1,4,5,6-tetrahydropyrimidin-2-ylcarbamoyl)-ethyl)-thiophene-2-carbonyl)-amino)-propionic Acid Isopropyl Ester

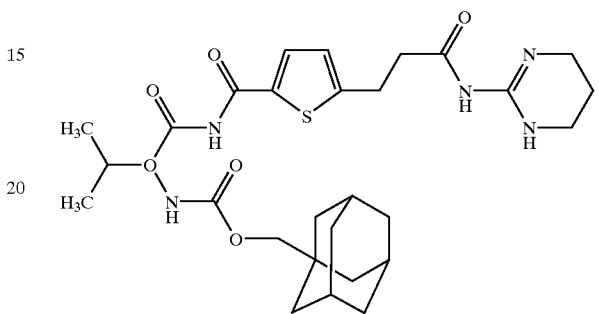

0.559 g (1 mmol) of (2S)-2-(1-adamantylmethoxycarbonylamino)-3-((5-(2-(1,4,5,6-tetrahydropyrimidin-2-ylcarbamoyl)-ethyl)-thiophene-2-carbonyl)-amino)-propionic acid (example 15) were dissolved in 10 ml of isopropanol. Under an inert gas atmosphere and under external cooling 0.26 ml of thionyl chloride were cautiously addded. After stirring for 8 hours at 50° C. the reaction was complete. The solvents were removed in vacuo to give a colourless foam which was purified by chromatography (silica gel; isopropanol/ethyl acetate/water (4/3/1; v/v/v)). The fractions containing the title compound were lyopholized to give 0.27 g of a colourless fluffy material.

Melting point: 160° C. (decomposition) Mass spectrum: m/e=602 (M+H$^+$).

Example 17

(2S)-2-(1-Adamantylmethoxycarbonylamino)-3-((5-(2-(1,4,5,6-tetrahydropyrimidin-2-ylcarbamoyl)-ethyl)-thiophene-2-carbonyl)-amino)-propionic Acid Isobutyl Ester

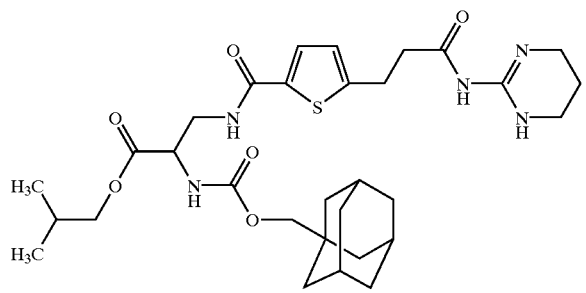

0.38 g (0.7 mmol) of (2S)-2-(1-adamantylmethoxycarbonylamino)-3-((5-(2-(1,4,5,6-tetrahydropyrimidin-2-ylcarbamoyl)-ethyl)-thiophene-2-carbonyl)-amino)-propionic acid (example 15) were dissolved in 7 ml of isobutanol. Under an inert gas atmosphere and under external ice cooling 0.19 ml of thionyl chloride were cautiously added. After stirring for 8 hours at room temperature the reaction was complete. The solvents were removed in vacuo to give a colourless foam which was purified by chromatography (silica gel; isopropanol/ethyl acetate/water (4/3/1; v/v/v)). The fractions containing the title compound were lyosphilized to give 0.30 g of a colourless solid.

Melting point: 210° C. (decomposition) Mass spectrum: m/e=616 (M+H$^+$).

Example 18

(2S)-3-((5-(2-(1,4,5,6-Tetrahydropyrimidin-2-ylcarbamoyl)-ethyl)-thiophene-2-carbonyl)-amino)-2-(2,4,6-trimethylphenyl-sulfonylamino)-propionic Acid

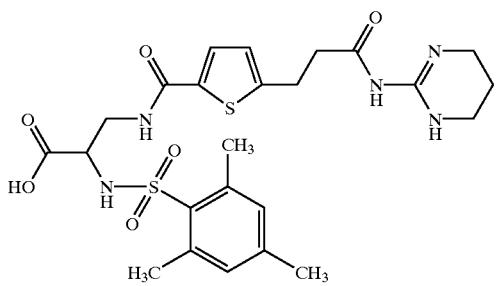

a) (2S)-3-((5-(2-Methoxycarbonyl-ethyl)-thiophene-2-carbonyl)-amino)-2-(2,4,6-trimethylphenyl-sulfonylamino)-propionic Acid tert-Butyl Ester 0.490 g (1.38 mmol) of (2S)-2-amino-3-((5-(2-methoxycarbonyl-ethyl)-thiophene-2-carbonyl)-amino)-propionic acid tert-butyl ester hydrochloride (example 15, step a) were dissolved in 15 ml of anhydrous dimethylformamide. Under stirring, 0.47 ml of N,N-diisopropyl-N-ethylamine and 0.302 g of 2,4,6-trimethylphenylsulfonyl chloride were added. Stirring was continued for 5 hours until the reaction was complete (thin layer chromatography). The solvents were removed in vacuo, and the residue was dissolved in ethyl acetate and washed with saturated sodium bicarbonate solution and with brine. After drying with anhydrous magnesium sulfate and filtration, the solvents were removed in vacuo to give 0.623 g of a yellow oil which was sufficiently pure for use in the subsequent step.

Mass spectrum: m/e=539 (M+H$^+$).

b) (2S)-3-((5-(2-(1,4,5,6-Tetrahydropyrimidin-2-ylcarbamoyl)-ethyl)-thiophene-2-carbonyl)-amino)-2-(2,4,6-trimethylphenyl-sulfonylamino)-propionic Acid tert-Butyl Ester 0.300 g of the compound obtained in step a) were dissolved in 5 ml of anhydrous dimethylformamide. After addition of 0.333 g of 2-amino-1,4,5,6-tetrahydropyrimidine the mixture was stirred for 6 hours at room temperature. TLC control showed that the reaction was complete. The solvent was removed in vacuo, and the residue was diluted with dichloromethane. The dichloromethane solution was washed five times with water and dried with anhydrous magnesium sulfate. After filtration, the solvents were removed in vacuo. The resulting oil (0.314 g) was sufficiently pure for use in the subsequent reaction step.

c) (2S)-3-((5-(2-(1,4,5,6-Tetrahydropyrimidin-2-ylcarbamoyl)-ethyl)-thiophene-2-carbonyl)-amino)-2-(2,4,6-trimethylphenyl-sulfonylamino)-propionic Acid 0.310 g (0.51 mmol) of the compound obtained in step b) were diluted with 10 ml of dichloromethane. Under stirring 2 ml of trifluoroacetic acid were added, and stirring was continued at room temperature for 1 hour. After addition of further 2 ml of trifluoroacetic acid and stirring for 2 hours the reaction was complete (TLC/HPLC). Evaporation of the solvents in vacuo gave a yellow resin which was diluted with 5 ml of glacial acetic acid. The solution was again evaporated to dryness in vacuo. This procedure was repeated once. The resulting resin was triturated with diethyl ether to give, after filtration, 0.272 g of a colourless amorphous solid.

Mass spectrum: m/e=550 (M+H$^+$).

According to the synthetic procedures described in example 18, the following compounds were prepared. If, in some cases, the product obtained in step b) was not sufficiently pure for use in the subsequent step, it was purified by fractionated chromatography (silica gel; ethyl acetate/methanol (1/1; v/v)).

Example 19

(2S)-2-(1-Naphthyl-sulfonylamino)-3-((5-(2-(1,4,5,6-tetrahydropyrimidin-2-ylcarbamoyl)-ethyl)-thiophene-2-carbonyl)-amino)-propionic Acid

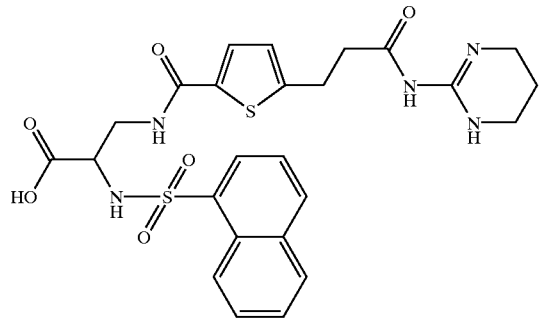

Mass spectrum: m/e=558 (M+H$^+$).

Example 20

(2S)-2-(n-Butyl-sulfonylamino)-3-((5-(2-(1,4,5,6-tetrahydropyrimidin-2-ylcarbamoyl)-ethyl)-thiophene-2-carbonyl)-amino)-propionic Acid

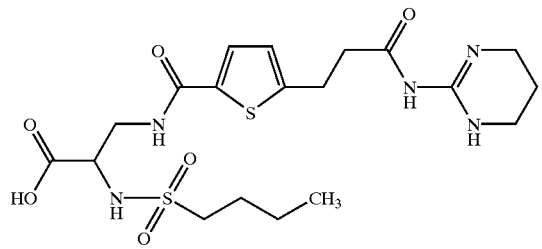

Mass spectrum: m/e=488 (M+H$^+$).

Example 21

(2S)-2-(8-Quinolyl-sulfonylamino)-3-((5-(2-(1,4,5,6-tetrahydropyrimidin-2-ylcarbamoyl)-ethyl)-thiophene-2-carbonyl)-amino)-propionic Acid

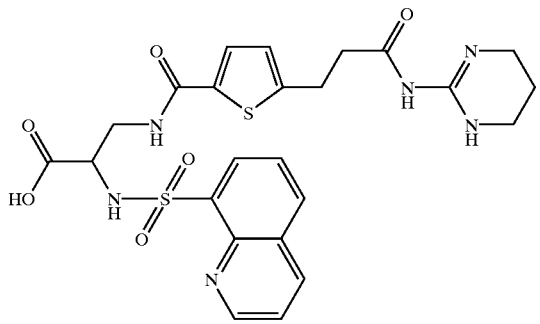

Mass spectrum: m/e=559 (M+H$^+$).

Example 22

(2S)-2-(4-Chlorophenyl-sulfonylamino)-3-((5-(2-(1,4,5,6-tetrahydropyrimidin-2-ylcarbamoyl)-ethyl)-thiophene-2-carbonyl)-amino)-propionic Acid

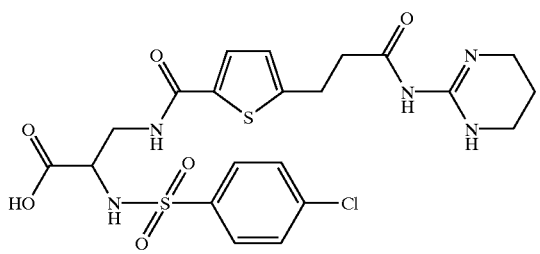

Mass spectrum: m/e=544 (M+H$^+$), 542 (M+H$^+$).

Example 23

(2S)-2-(4-Biphenylyl-sulfonylamino)-3-((5-(2-(1,4,5,6-tetrahydropyrimidin-2-ylcarbamoyl)-ethyl)-thiophene-2-carbonyl)-amino)-propionic Acid

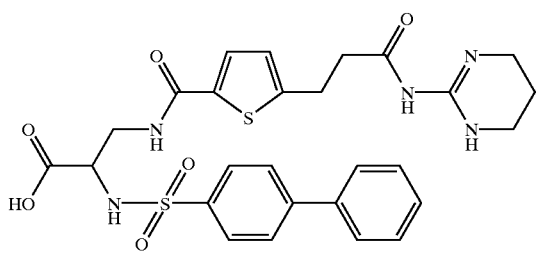

Mass spectrum: m/e=584 (M+H$^+$).

Analogously to the above examples the compounds of examples 24 to 26 were synthesized.

Example 24

(3RS)-3-(Benzo[1,3]dioxol-5-yl)-3-((5-(2-(1,4,5,6-tetrahydropyrimidin-2-ylcarbamoyl)-ethyl)-thiophene-2-carbonyl)-amino)-propionic Acid

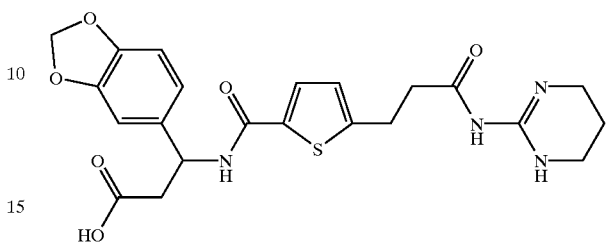

Mass Spectrum: m/e=473 (M+H$^+$).

Example 25

(3RS)-3-(Benzo[1,3]dioxol-5-yl)-3-((5-(2-(1,4,5,6-tetrahydropyrimidin-2-ylcarbamoyl)-cyclopropyl)-thiophene-2-carbonyl)-amino)-propionic Acid

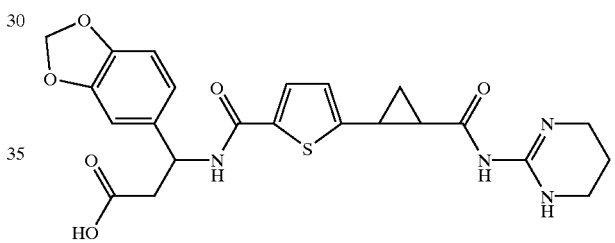

Mass spectrum: m/e=485 (M+H$^+$).

Example 26

(2S)-2-(1-Adamantylmethoxycarbonylamino)-3-((5-(2-(1,4,5,6-tetrahydropyrimidin-2-ylcarbamoyl)-vinyl)-thiophene-2-carbonyl)-amino)-propionic Acid

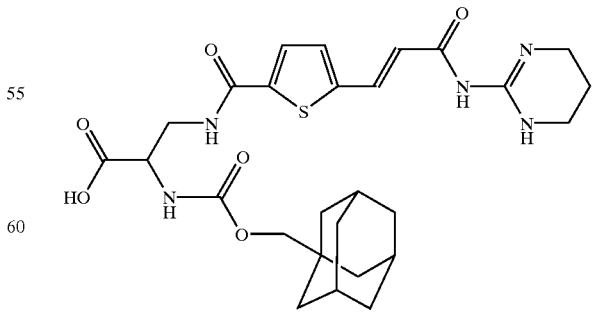

Mass spectrum: m/e=558 (M+H$^+$).

Example 27

(2S)-3-((5-(2-(1,4,5,6-Tetrahydropyrimidin-2-ylcarbamoyl)-ethyl-thiophene-2-carbonyl)-amino)-2-(4-trifluoromethylphenyl-sulfonylamino)-propionic Acid

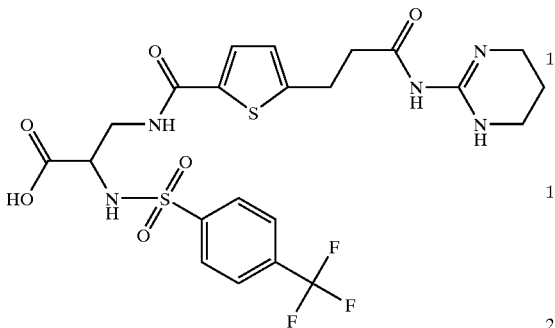

a) (2S)-3-((5-(2-Methoxycarbonyl-ethyl)-thiophene-2-carbonyl)-amino)-2-(4-trifluoromethylphenyl-sulfonylamino)-propionic Acid tert-Butyl Ester A solution of 0.197 g (0.5 mmol) of (2S)-2-amino-3-((5-(2-methoxycarbonyl-ethyl)-thiophene-2-carbonyl)-amino)-propionic acid tert-butyl ester hydrochloride (example 15, step a) and triethylamine (0.14 ml, 1 mmol) in dichloromethane (5 ml) was cooled to 0° C. in an ice bath and a solution of 0.250 g (1 mmol) of 4-trifluoromethylphenylsulfonyl chloride in dichloromethane (5 ml) was added. Then the reaction mixture was stirred for 3 hours at room temperature. After removal of the solvent in vacuo the residue was absorbed onto silica gel and chromatographed with ethyl acetate/cyclohexane (1/1) to yield 0.127 g (45%) of the title compound as a white amorphous solid.

$^1$H NMR (CDCl$_3$): δ (ppm)=1.27 (s, 9H), 2.70 (t, 2H) and 3.15 (t, 2H) (ester-CH$_2$—CH$_2$-thienyl), 3.51 and 3.85 (m, 2H, CH$_2$—CH), 3.71 (s, 3H, OCH$_3$), 3.75 (m, 1H, CH$_2$—CH), 5.92 (1H, NH), 6.40 (t, 1H, NH), 6.81 and 7.38 (2d, 2H, thienyl-3,4H), 7.75 and 7.90 (aromatic protons).

Mass spectrum: m/e=565 (M+H$^+$).

b) (2S)-3-((5-(2-(1,4,5,6-Tetrahydropyrimidin-2-ylcarbamoyl)-ethyl)-thiophene-2-carbonyl-amino)-2-(4-trifluoromethylphenyl-sulfonylamino)-propionic Acid tert-Butyl Ester 0.120 g (0.21 mmol) of the compound obtained in step a) were dissolved in 1.5 ml of tetrahydrofuran. After addition of 46 mg (0.46 mmol) of 2-amino-1,4,5,6-tetrahydropyrimidine the mixture was stirred for 1.75 h at room temperature. TLC control showed that the reaction was not complete. Then 60 mg (0.60 mmol) of 2-amino-1,4,5,6-tetrahydropyrimidine were added and the reaction mixture was stirred again for 1 h at room temperature. The mixture was absorbed onto silica gel. Chromatography (ethyl acetate/chloroform/methanol/water/acetic acid, 0.5/0.35/0.15/0.03/0.015) gave the title compound (0.117 g, 87%) as a white amorphous solid.

$^1$H NMR (CDCl$_3$): δ (ppm)=1.28 (s, 9H), 1.96 (m, 2H), 2.87 (t, 2H) and 3.16 (t, 2H) (ester-CH$_2$—CH$_2$-thienyl), 3.41 (t, 4H) and 3.74 (m, 2H, CH$_2$—CH), 4.02 (t, 1H, CH$_2$—CH), 6.70 (t, 1H, NH), 6.80 and 7.34 (2d, 2H, thienyl-3,4H), 7.72 and 7.93 (aromatic protons) Mass spectrum: m/e=632 (M+H$^+$).

c) (2S)-3-((5-(2-(1,4,5,6-Tetrahydropyrimidin-2-ylcarbamoyl)-ethyl)-thiophene-2-carbonyl)-amino)-2-(4-trifluoromethylphenyl-sulfonylamino)-propionic Acid 0.096 g (0.15 mmol) of the compound obtained in step b) were dissolved in dichloromethane (1 ml). Trifluoroacetic acid (1 ml) was added and the reaction mixture was stirred for 3 h at room temperature. After evaporation of the solvents lyophilization gave the title compound (0.75 g, 86%) as a white amorphous solid.

$^1$H NMR (D$_6$-DMSO): δ (ppm)=1.86 (m, 2H), 2.79 (t, 2H) and 3.08 (t, 2H) (ester-CH$_2$—CH$_2$-thienyl), 3.36 (m, 4H), 3.35 and 3.48 (m, 2H, CH$_2$—CH), 4.06 (m, 1H, CH$_2$—CH), 6.87 and 7.43 (2d, 2H, thienyl-3,4H), 7.79 and 7.95 (aromatic protons), 8.41 (t, 1H, NH), 8.51 (d, 1H, NH) Mass spectrum: m/e=576 (M+H$^+$).

Analogously to example 27 the compounds of examples 28 to 31 were synthezised.

Example 28

(2S)-3-((5-(2-(1,4,5,6-Tetrahydropyrimidin-2-ylcarbamoyl)-ethyl)-thiophene-2-carbonyl)-amino)-2-(2,2,2-trifluoroethyl-sulfonylamino)-propionic Acid

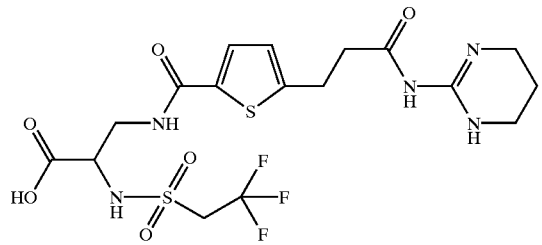

$^1$H NMR (D$_6$-DMSO): δ (ppm)=1.85 (m, 2H), 2.80 (t, 2H) and 3.09 (t, 2H) (ester-CH$_2$—CH$_2$-thienyl), 3.35 (m, 4H), 3.40–3.65 (m, 2H, CH$_2$—CH), 4.19 (m, 1H, CH$_2$—CH), 4.30–4.50 (m, 2H, CH$_2$—CF$_3$), 6.91 and 7.54 (2d, 2H, thienyl-3,4H), 8.45 (t, 1H, NH), 8.50 (m, 1H, NH) Mass spectrum: m/e=514 (M+H$^+$).

Example 29

(2S)-2Ethenyl-sulfonylamino)-3-((5-(2-(1,4,5,6-tetrahydropyrimidin-2-ylcarbarmoyl)-ethyl)-thiophene-2-carbonyl)-amino)-propionic Acid

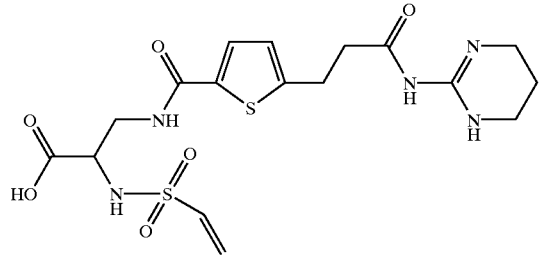

$^1$H NMR (D$_6$-DMSO): δ (ppm)=1.85 (m, 2H), 2.81 (t, 2H) and 3.09 (t, 2H) (ester-CH$_2$—CH$_2$-thienyl), 3.36 (m, 4H), 3.42–3.53 (m, 2H, C$\underline{H}_2$—CH), 3.96 (m, 1H, CH$_2$—C$\underline{H}$), 5.83–5.99 (d, 2H, C$\underline{H}_2$=CH), 6.64 (dd, 1H, CH$_2$=C$\underline{H}$), 6.92 and 7.55 (2d, 2H, thienyl-3,4H), 7.91 (d, 1H, NH), 8.51 (m, 1H, NH) Mass spectrum: m/e=458 (M+H$^+$).

Example 30

(2S)-2-(3-Chloropropyl-sulfonylamino)-3-((5-(2-(1,4,5,6-tetrahydropyrimidin-2-ylcarbamoyl)-ethyl)-thiophene-2-carbonyl)-amino)-propionic Acid

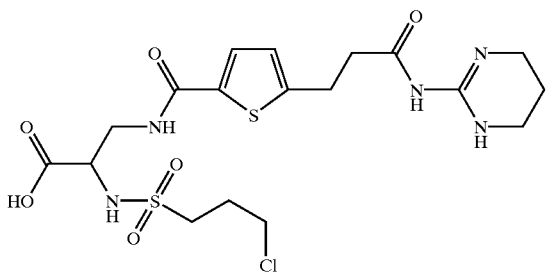

$^1$H NMR (D$_6$-DMSO): δ (ppm)=1.85 (m, 2H), 2.11 (m, 2H), 2.91 (t, 2H) and 3.09 (t, 2H) (ester-C$\underline{H}_2$—C$\underline{H}_2$-thienyl), 3.09 (m, 2H), 3.30 (m, 4H), 3.43–3.54 (m, 2H, C$\underline{H}_2$—CH), 3.65 (t, 2H, CH$_2$SO$_2$), 4.11 (m, 1H, CH$_2$—C$\underline{H}$), 6.91 and 7.54 (2d, 2H, thienyl-3,4H), 7.93 (d, 1H, NH), 8.51 (m, 1H, NH) Mass spectrum: m/e=508 (M+H$^+$).

Example 31

(2S)-2-(Chloromethyl-sulfonylamino)-3((5-(2-(1,4,5,6-tetrahydropyrimidin-2-ylcarbamoyl)-ethyl)-thiophene-2-carbonyl)-amino)-propionic Acid

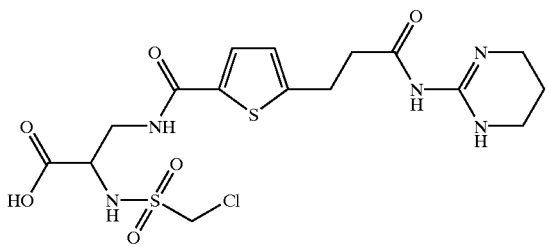

$^1$H NMR (D$_6$-DMSO): δ (ppm)=1.86 (m, 2H), 2.81 (t, 2H) and 3.09 (t, 2H) (ester-CH$_2$—CH$_2$-thienyl), 3.42 (m, 4H), 3.52 (m, 2H, C$\underline{H}_2$—CH), 4.18 (m, 1H, CH$_2$—C$\underline{H}$), 4.86 (AB, 2H), 6.91 and 7.56 (2d, 2H, thienyl-3,4H), 8.30 (d, 1H, NH), 8.49 (m, 1H, NH). Mass spectrum: m/e=480 (M+H$^+$).

Example 32

(2S)-2-(4-tert-Butylphenyl-sulfonylamino)-3-((5-(2-(1,4,5,6-tetrahydropyrimidin-2-ylcarbamoyl)-ethyl)-thiophene-2-carbonyl)-amino)-propionic Acid

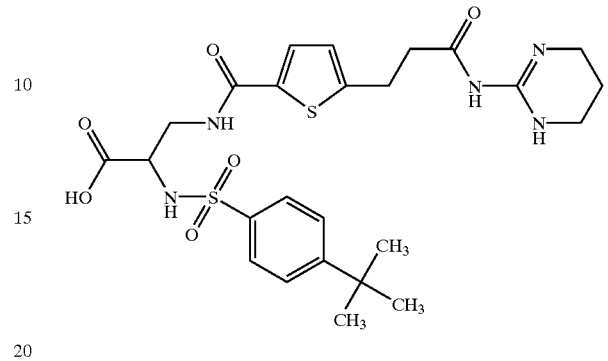

a) (2S)-2-(4-tert-Butylphenyl-sulfonylamino)-3-((5-(2-methoxycarbonyl-ethyl)-thiophene-2-carbonyl)-amino)-propionic Acid tert-Butyl Ester A solution of 0.395 g (1 mmol) of (2S)-2-amino-3-((5-(2-methoxycarbonyl-ethyl)-thiophene-2-carbonyl)-amino)-propionic acid tert-butyl ester hydrochloride (example 15, step a) and triethylamine (0.15 ml, 1.1 mmol) in dichloromethane (10 ml) was cooled to 0° C. in an ice bath and a solution of 0.255 g (1.1 mmol) of 4-tert-butylphenylsulfonyl chloride in dichloromethane (5 ml) was added. Then the reaction mixture was stirred at room temperature overnight. After removal of the solvent in vacuo the residue was absorbed onto silica gel and chromatographed with ethyl acetate/cyclohexane (1/1) to yield 0.285 g (52%) of the title compound as a white amorphous solid.

$^1$H NMR (CDCl$_3$): δ (ppm)=1.27 (s, 9H), 1.31 (s, 9H), 2.70 and 3.17 (AA'BB', 2×2H, ester-C$\underline{H}_2$—C$\underline{H}_2$-thienyl), 3.51 and 3.88 (m, 2H, C$\underline{H}_2$—CH), 3.71 (s, 3H, OCH$_3$), 3.85 (m, 1H, CH$_2$—C$\underline{H}$), 5.58 (1H, NH), 6.53 (t, 1H, NH), 6.81 and 7.38 (2d, 2H, thienyl-3,4H), 7.50 and 7.77 (aromatic protons).

b) (2S)-2-(4-tert-Butylphenyl-sulfonylamino)-3-((5-(2-(1,4,5,6-tetrahydropyrimidin-2-ylcarbamoyl)-ethyl)-thiophene-2-carbonyl)-amino)-propionic Acid tert-Butyl Ester 0.285 g (0.52 mmol) of the compound obtained in step a) were dissolved in 3 ml of tetrahydrofuran. After addition of 0.103 g (1.04 mmol) of 2-amino-1,4,5,6-tetrahydropyrimidine the mixture was stirred for 1 h at room temperature. TLC control showed that the reaction was not complete. Then 0.103 g (1.04 mmol) of 2-amino-1,4,5,6-tetrahydropyrimidine were added and the reaction mixture was stirred again for 1 h at room temperature. The mixture was absorbed onto silica gel. Chromatography (ethyl acetate/chloroform/methanol/water/acetic acid, 0.5/0.35/0.15/0.03/0.015) gave the title compound (0.27 g, 84%) as a white amorphous solid.

Mass spectrum: m/e=620 (M+H$^+$).

c) (2S)-2-(4-tert-Butylphenyl-sulfonylamino)-3-((5-(2-(1,4,5,6-tetrahydropyrimidin-2-ylcarbamoyl)-ethyl)-thiophene-2-carbonyl)-amino)-propionic Acid 0.27 g (0.43 mmol) of the compound obtained in step b) were dissolved in dichloromethane (1 ml). Trifluoroacetic acid (1 ml) was added and the reaction mixture was stirred for 2 h at room temperature. After evaporation of the solvents lyophilization gave the title compound (0.25 g, 86%) as a white amorphous solid.

Mass spectrum: m/e=564 (M+H⁺).

Analogously to example 32 the compounds of examples 33 to 35 were synthesized.

Example 33

(2S)-2-(4-Isopropylphenyl-sulfonylamino)-3-((5-(2-(1,4,5,6-tetrahydropyrimidin-2-ylcarbamoyl)-ethyl)-thiophene-2-carbonyl)-amino)-propionic Acid

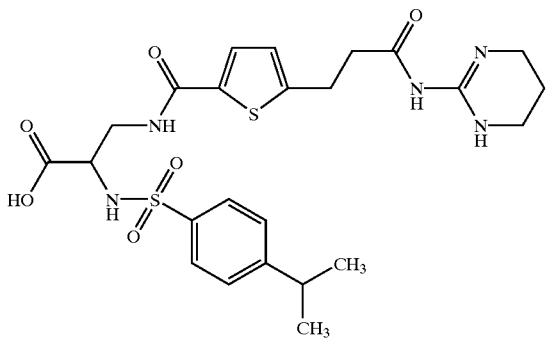

Mass spectrum: m/e=550 (M+H⁺).

Example 34

(2S)-2-(Methyl-sulfonylamino)-3-((5-(2-(1,4,5,6-tetrahydropyrimidin-2-ylcarbamoyl)-ethyl)-thiophene-2-carbonyl)-amino)-propionic Acid

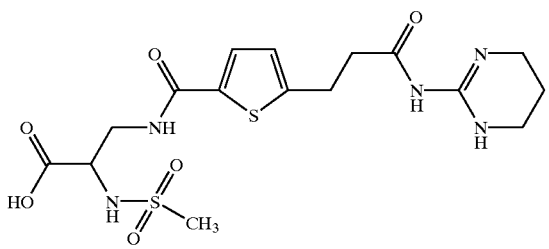

Mass spectrum: m/e=446 (M+H⁺).

Example 35

(2S)-2-(n-Propyl-sulfonylamino)-3-((5-(2-(1,4,5,6-tetrahydropyrimidin-2-ylcarbamoyl)-ethyl)-thiophene-2-carbonyl)-amino)-propionic Acid

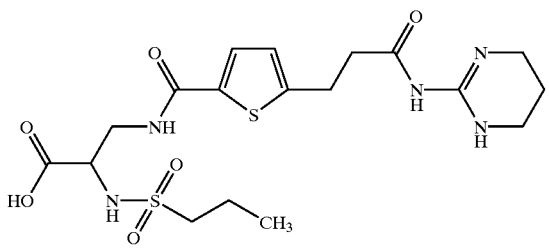

Mass spectrum: m/e=474 (M+H⁺).

Pharmacological Testing

The inhibition of bone resorption by the compounds according to the invention can be determined, for example, with the aid of an osteoclast resorption test ("PIT ASSAY"), for example analogously to WO-A-95/32710.

The inhibitory action of the compounds according to the invention against the vitronectin receptor $\alpha_v\beta_3$ can be determined, for example, by the tests described below.

A) Test for the Measurement of the Inhibition of the Binding of Kistrin to Human Vitronectin Receptor (VnR) (Abbreviated as K/VnR Test)

1. Purification of Kistrin

Kistrin was purified using the methods of Dennis et al., as described in Proc. Natl. Acad. Sci. USA 1989, 87, 2471–2475 and PROTEINS: Structure, Function and Genetics 1993, 15, 312–321.

2. Purification of Human Vitronectin Receptor

Human vitronectin receptor was isolated from human placenta using the method of Pytela et al., Methods Enzymol. 1987, 144, 475. Human vitronectin receptor ($\alpha_v\beta_3$) can also be isolated from some cell lines (for example from 293 cells, a human embryonic kidney cell line) which are cotransfected with DNA sequences for the two subunits, $\alpha_v$ and $\beta_3$, of the vitronectin receptor. The subunits were extracted with octylglycoside and subsequently chromatographed on concanavalin A, heparin-Sepharose and S-300.

3. Monoclonal Antibodies

Murine monoclonal antibodies which are specific for the $\beta_3$ subunit of the vitronectin receptor were prepared either by the method of Newman et al., Blood, 1985, 227–232, or by a similar method. The rabbit Fab 2 anti-mouse Fc conjugate with horseradish peroxidase (anti-mouse Fc HRP) was obtained from Pel Freeze (Catalog No. 715 305-1).

4. ELISA Test

The ability of substances to inhibit the binding of Kistrin to the vitronectin receptor was elucidated using an ELISA test. For this purpose, Nunc 96-well microtiter plates were coated with a solution of kistrin (0.002 mg/ml) in accordance with the method of Dennis et al., as described in PROTEINS: Structure, Function and Genetics 1993, 15, 312–321. The plates were washed twice with PBS/0.05% Tween 20 and blocked by incubating them (for 60 min) with bovine serum albumin (BSA, 0.5%, RIA grade or better) in tris-HCl (50 mM), NaCl (100 mM), MgCl₂ (1 mM), CaCl₂ (1 mM), MnCl₂ (1 mM), pH 7. Solutions of known inhibitors and of the test substances, in concentrations of $2\times10^{-12}$ to $2\times10^{-6}$ mol/l, were prepared in assay buffer (BSA, 0.5%, RIA grade or better, in tris-HCl (50 mM), NaCl (100 mM), MgCl₂ (1 mM), CaCl₂ (1 mM), MnCl₂ (1 mM), pH 7). The blocked plates were emptied and in each case 0.025 ml of this solution, which contained a defined concentration (from $2\times10^{-12}$ to $2\times10^{-6}$ mol/l) of either a known inhibitor or a test substance, was added to each well. 0.025 ml of a solution of the vitronectin receptor in the test buffer (0.03 mg/ml) was pipetted into each well of the plate, and the plate was then incubated at room temperature on a shaker for 60 to 180 min. In the meantime, a solution (6 ml/plate) of a murine monoclonal antibody specific for the $\beta_3$ subunit of the vitronectin receptor was prepared in the assay buffer (0.0015 mg/ml). A second rabbit antibody, which represents an anti-mouse Fc HRP antibody conjugate, was added to this solution (0.001 ml of stock solution/6 ml of the murine monoclonal anti-$\beta_3$ antibody solution), and this mixture of the murine anti-$\beta_3$ antibody and the rabbit anti-mouse Fc HRP antibody conjugate was allowed to incubate while the receptor/inhibitor incubation was in progress. The test plates were washed 4 times with PBS solution containing 0.05% Tween-20, and 0.05 ml of the antibody mixture was in each case pipetted into each well of the plate which was then incubated for 60 to 180 min. The plate was washed 4 times with PBS/0.05%

Tween-20 and then developed with 0.05 ml/well of a PBS solution which contained 0.67 mg/ml o-phenylenediamine and 0.012% $H_2O_2$. Alternatively, o-phenylenediamine can be used in a buffer (pH 5) which contains $Na_3PO_4$ (50 mM) and citric acid (0.22 mM). The color development was stopped with 1N $H_2SO_4$ (0.05 ml/well). The absorption of each well was measured at 492–405 nm and the data were evaluated using standard methods.

B) Test for the Measurement of the Inhibition of Binding of 293 Cells to Human Vitronectin (Vn) (Abbreviated as Vn/293 Cell Test)

1. Purification of Human Vitronectin

Human vitronectin was isolated from human plasma and purified by affinity chromatography according to the method of Yatohgo et al., Cell Structure and Function, 1988, 23, 281–292.

2. Cell Test 293 cells, a human embryonic kidney cell line, which were cotransfected with DNA sequences for the $\alpha_v$ and $\beta_3$ subunits of the vitronectin receptor $\alpha_v\beta_3$, were selected for a high rate of expression (>500,000 $\alpha_v\beta_3$ receptors/cell) according to the FACS method. The selected cells were cultured and sorted again by means of FACS in order to obtain a stable cell line (15 D) with expression rates>1,000,000 copies of $\alpha_v\beta_3$ per cell.

A Linbro 96-well tissue culture plate with a flat bottom was coated overnight at 4° C. with human vitronectin (0.01 mg/ml, 0.05 ml/well) in phosphate-buffered saline solution (PBS) and then blocked with 0.5% strength BSA (bovine serum albumin). Solutions of the test substances from $10^{-10}$ mol/l to $2 \times 10^{-3}$ mol/l in glucose-containing DMEM medium were prepared and 0.05 ml/well of the solution were added to the plate in each case. The cells which expressed high levels of $\alpha_v\beta_3$ (for example 15 D) were suspended in glucose-containing DMEM medium and the suspension was adjusted to a content of 25,000 cells/0.05 ml of medium. 0.05 ml of this cell suspension was added to each well and the plate was incubated at 37° C. for 90 min. The plate was washed 3 times with warm PBS in order to remove unbound cells. The bound cells were lyzed in citrate buffer (25 mM, pH 5.0) which contained 0.25% Triton X-100. The hexoseamidase substrate p-nitrophenyl-N-acetyl-β-D-glucosaminide was then added and the plate was incubated at 37° C. for 90 min. The reaction was stopped with a glycine (50 mM)/EDTA (5 mM) buffer (pH 10.4) and the absorption of each well was measured at 405 to 650 nm. The data were analyzed according to standard methods.

The following test results were obtained.

| Compound | K/VnR test $IC_{50}$ ($\mu$M) | Vn/293 cell test $IC_{50}$ ($\mu$M) |
| --- | --- | --- |
| Example 1 | 0.039 | 0.837 |
| Example 2 | 0.0068 | 0.063 |
| Example 3 | 0.060 | 0.041 |
| Example 4 | 0.0098 | 0.069 |
| Example 5 | 0.0089 | 1.43 |
| Example 6 | 0.035 | 3.61 |
| Example 7 | 0.033 | >10 |
| Example 8 | 0.120 | |
| Example 9 | 0.175 | |
| Example 10 | 0.069 | 11.48 |
| Example 11 | 0.175 | 20.89 |
| Example 12 | 0.8 | 40.74 |
| Example 13 | 0.032 | >5 |
| Example 14 | >10 | |
| Example 15 | 0.0021 | 0.026 |
| Example 18 | 0.0015 | 0.010 |
| Example 19 | 0.0021 | 0.013 |

-continued

| Compound | K/VnR test $IC_{50}$ ($\mu$M) | Vn/293 cell test $IC_{50}$ ($\mu$M) |
| --- | --- | --- |
| Example 20 | 0.0037 | 0.090 |
| Example 21 | 0.003 | 0.047 |
| Example 22 | 0.0023 | 0.012 |
| Example 23 | 0.0025 | 0.026 |
| Example 24 | 0.0095 | 1.73 |
| Example 25 | 0.016 | >5 |
| Example 26 | 1.10 | |
| Example 27 | 0.002 | |
| Example 28 | 0.005 | |
| Example 29 | 0.018 | |
| Example 30 | 0.0019 | |
| Example 31 | 0.004 | |
| Example 32 | 0.0027 | 0.012 |
| Example 33 | 0.0022 | 0.006 |
| Example 34 | 0.0047 | 0.069 |
| Example 35 | 0.0035 | 0.022 |

What is claimed is:

1. A compound selected from the group consisting of a compound of the formula

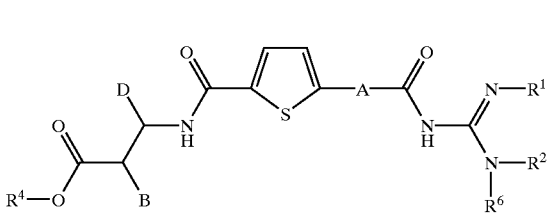

I wherein A is selected from the group consisting of saturated and unsaturated bivalent alkylene of up to 9 carbon atoms and bivalent cycloalkylene of 3 to 7 carbon atoms, both unsubstituted or substituted with at least one member of the group consisting of halogen, alkyl of 1 to 6 carbon atoms, alkoxy of 1 to 6 carbon atoms, aryl of 6 to 14 carbon atoms, aralkyl of 6 to 14 aryl carbon atoms and 1 to 6 alkyl carbon atoms, heteroaryl of 5 to 14 carbon atoms, heteroarylalkyl of 5 to 14 hetero carbon atoms and 1 to 6 alkyl carbon atoms, cycloalkyl of 3 to 12 carbon atoms, oxo and cycloalkylalkyl of 3 to 12 cycloalkyl carbon atoms and 1 to 6 alkyl carbon atoms, B is selected from the group consisting of hydrogen, —NH—CO—OR$^5$—NH—SO$_2$—R$^5$, —NH—SO-Aryl of 6 to 14 carbon atoms, —NH—SO$_2$-heteroaryl of 5 to 14 carbon atoms, —NH—CO—R$^5$, —NO—CO-Aryl of 6 to 14 carbon atoms, —NH—CO-heteroaryl of 5 to 14 carbon atoms, —NH—CO—NH—R$^5$, —NH—CO—NH-aryl of 6 to 14 carbon atoms, —NH—CO—NH-heteroaryl of 5 to 14 carbon atoms, —NH—SO$_2$—NH—R$^5$, —NH—SO$_2$—NH-aryl of 6 to 14 carbon atoms and —NH—SO$_2$—NH-heteroaryl of 5 to 14 carbon atoms, D is selected from the group consisting of hydrogen, aryl of 6 to 14 carbon atoms, heteroaryl of 5 to 14 carbon atoms and R$^5$, R$^1$ and R$^2$ are individually hydrogen or unsubstituted or substituted alkyl of 1 to 6 carbon atoms with the substituents being at least one R$^3$, R$^3$ is selected from the group consisting of alkyl of 1 to 8 carbon atoms, alkoxy of 1 to 8 carbon atoms, aryl of 6 to 14 carbon atoms, aralkyl of 6 to 14 aryl carbon atoms and 1 to 6 alkyl carbon atoms, halogen, —CF$_3$, —OH, —NO$_2$ and —NH$_2$, R$^4$ is selected from the group consisting of hydrogen, Alk-COO-Alk' and alkyl of 1 to 6 carbon atoms unsubstituted or substituted with a member selected from the group consisting of —OH, alkoxy of 1 to 4 carbon atoms, alkyl SO$_2$— of 1 to 4 carbon atoms,

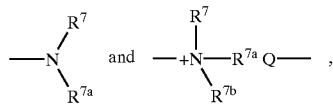 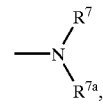

Alk is alkyl of 1 to 6 carbon atoms, Alk' is alkyl of 1 to 4 carbon atoms, $R^7$, $R^{7a}$ and $R^{7b}$ are individually selected from the group consisting of hydrogen, alkyl of 1 to 6 carbon atoms, aryl of 6 to 14 carbon atoms and aralkyl of 6 to 14 aryl carbon atoms and 1 to 6 alkyl carbon atoms, Q— is a pharmaceutically acceptable anion or $R^4$ is selected from the group consisting of

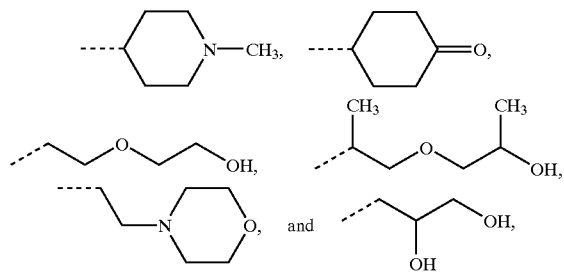

$R^5$ is selected from the group consisting of alkyl of 1 to 14 carbon atoms unsubstituted or substituted with at least one halogen, cycloalkyl of 3 to 12 carbon atoms, cycloalkylalkyl of 3 to 12 cycloalkyl carbon atoms and 1 to 6 alkyl carbon atoms, aralkyl of 6 to 14 aryl carbon atoms and 1 to 6 alkyl carbon atoms and heteroarylalkyl of 5 to 14 aryl carbon atoms and 1 to 6 alkyl carbon atoms, the aryl and heteroaryl being unsubstituted or substituted with at least one $R^3$, $R^6$ is selected from the group consisting of hydrogen, —OH, —NO$_2$, alkyl-OCO— of 1 to 6 carbon atoms and alkyl-O—CO—O— of 1 to 6 carbon atoms in all stereoisomeric forms and mixtures thereof and its non-toxic, pharmaceutically acceptable addition salts with a base or acid.

2. A compound of claim 1 wherein A is selected from the group consisting of saturated or unsaturated bivalent alkylene of 1 to 5 carbon atoms and bivalent cycloalkylene of 3 to 5 carbon atoms, both individually unsubstituted or substituted with 1 to 2 members selected from the group consisting of halogen, alkyl of 1 to 6 carbon atoms, alkoxy of 1 to 6 carbon atoms, aryl of 6 to 14 carbon atoms, aralkyl of 6 to 14 aryl carbon atoms and 1 to 6 alkyl carbon atoms, heteroaryl of 5 to 14 carbon atoms, heteroarylalkyl of 5 to 14 heteroaryl carbon atoms and 1 to 6 alkyl carbon atoms, cycloalkyl of 3 to 12 carbon atoms, oxo and cycloalkylalkyl of 3 to 12 cycloalkyl carbon atoms and 1 to 6 alkyl carbon atoms, B is selected from the group consisting of hydrogen, —NH—CO—OR$^5$, —NH—SO$_2$-alkyl of 1 to 14 carbon atoms unsubstituted or substituted by at least one halogen, —NH—SO$_2$-aryl of 6 to 14 carbon atoms and —NH$_2$—SO$_2$-heteroaryl of 5 to 14 carbon atoms, D is selected from the group consisting of hydrogen, aryl of 6 to 14 carbon atoms, heteroaryl of 5 to 14 carbon atoms and $R_1$ and $R_2$ are hydrogen, $R^3$ is alkyl of 1 to 4 carbon atoms or alkoxy of 1 to 4 carbon atoms, $R^4$ is hydrogen or alkyl of 1 to 6 carbon atoms unsubstituted or substituted with a member selected from the group consisting of alkoxy of 1 to 4 carbon atoms, alkyl-SO$_2$— of 1 to 4 carbon atoms and

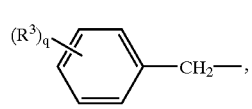

$R^7$ and $R^{7a}$ are individually hydrogen or alkyl of 1 to 4 carbon atoms, $R^5$ is selected from the group consisting of alkyl of 1 to 10 carbon atoms, cycloalkyl of 3 to 12 carbon atoms, cycloalkylalkyl of 3 to 12 cycloalkyl carbon atoms and 1 to 6 alkyl carbon atoms and $$\underset{(R^3)_q}{\overset{}{\underset{}{\bigcirc}}}-CH_2- \qquad II$$

q is 0 or 1, $R^6$ is hydrogen or —CO—O-alkyl of 1 to 6 carbon atoms and its non-toxic pharmaceutically acceptable salts.

3. A compound of claim 1 wherein A is a saturated or unsaturated bivalent alkylene of 1 to 3 carbon atoms or a bivalent cycloalkylene of 3 to 5 carbon atoms, both unsubstituted or substituted with 1 to 2 members of the group consisting of fluorine, chlorine, bromine, alkyl of 1 to 6 carbon atoms, alkoxy of 1 to 6 carbon atoms, aryl of 6 to 14 carbon atoms, aralkyl of 6 to 14 aryl carbon atoms and 1 to 6 alkyl carbon atoms, heteroaryl of 5 to 14 carbon atoms, heteroarylalkyl of 5 to 14 heteroaryl carbon atoms and 1 to 6 alkyl carbon atoms, cycloalkyl of 3 to 12 carbon atoms, oxo and cycloalkylalkyl of 3 to 12 cycloalkyl carbon atoms and 1 to 6 alkyl carbon atoms, B is selected from the group consisting of hydrogen, —NH—CO—OR$^5$, —NH—SO$_2$-alkyl of 1 to 14 carbon atoms unsubstituted or substituted by at least one halogen, —NH—SO$_2$-aryl of 6 to 14 carbon atoms and —NH—SO$_2$-heteroaryl of 5 to 14 carbon atoms, D is selected from the group consisting of hydrogen, aryl of 6 to 14 carbon atoms and heteroaryl of 5 to 14 carbon atoms, $R^1$ and $R^2$ are hydrogen, $R^3$ is alkyl of 1 to 4 carbon atoms or alkoxy of 1 to 4 carbon atoms, $R^4$ is hydrogen or alkyl of 1 to 6 carbon atoms, $R^5$ is selected from the group consisting of alkyl of 1 to 7 carbon atoms, cycloalkyl of 6 to 12 carbon atoms, cycloalkylalkyl of 6 to 12 carbon atoms, cycloalkylalkyl of 6 to 12 cycloalkyl carbon atoms and 1 to 6 alkyl carbon atoms and

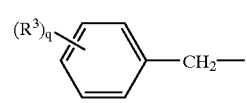

q is 0 or 1, $R^6$ is hydrogen or —CO—O-alkyl of 1 to 4 carbon atoms and its pharmaceutically acceptable salts.

4. A compound of claim 1 wherein A is a saturated or unsaturated, bivalent alkylene of 1 to 3 carbon atoms or a bivalent cycloalkylene of 3 to 5 carbon atoms, B is selected from the group consisting of hydrogen, —NH—CO—OR$^5$, —NH—SO$_2$-alkyl of 1 to 14 carbon atoms unsubstituted or substituted by at least one halogen, —NH—SO$_2$-aryl of 6 to 14 carbon atoms and —NH$_2$—SO$_2$-heteroaryl of 5 to 14 carbon atoms, $R^1$ and $R^2$ are hydrogen, $R^3$ is alkyl of 1 to 4 carbon atoms or alkoxy of 1 to 4 carbon atoms, $R^4$ is hydrogen or alkyl of 1 to 4 carbon atoms, $R^5$ is selected from the group consisting of alkyl of 1 to 7 carbon atoms, cycloalkyl of 6 to 12 carbon atoms, cycloalkylalkyl of 6 to 12 cycloalkyl carbon atoms and 1 to 4 alkyl carbon atoms and

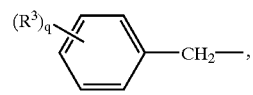

q is 0 or 1, $R^6$ is hydrogen or —CO—O-Alkyl of 1 to 4 carbon atoms, its pharmaceutically acceptable salts.

5. A method of inhibiting tumor growth in warm-blooded animals comprising administering to warm-blooded animals a tumor growth inhibiting amount of a compound of claim 1.

6. A method of treating osteoporosis in warm-blooded animals comprising administering to warm-blooded animals an amount of a compound of claim 1 sufficient to treat osteoporosis.

7. A method of treating inflammation in warm-blooded animals comprising administering to warm-blooded animals an anti-inflammatorily effective amount of a compound of claim 1.

8. A method of treating cardiovascular disorders in warm-blooded animals comprising administering to warm-blooded animals an amount of a compound of claim 1 sufficient to treat cardiovascular disorders.

* * * * *